US012364782B2

(12) United States Patent
Zanata et al.

(10) Patent No.: US 12,364,782 B2
(45) Date of Patent: Jul. 22, 2025

(54) APPARATUS FOR THE STERILIZATION OF AMBIENT AIR BY MEANS OF A LASER RAYS FILTER

(71) Applicant: KAIRLASER S.R.L., Villorba (IT)

(72) Inventors: Francesco Zanata, Ponzano Veneto (IT); Serena Zacchigna, Ponzano Veneto (IT)

(73) Assignee: KAIRLASER S.R.L., Villorba (IT)

( * ) Notice: Subject to any disclaimer, the term of this patent is extended or adjusted under 35 U.S.C. 154(b) by 380 days.

(21) Appl. No.: 18/011,891

(22) PCT Filed: Jun. 23, 2021

(86) PCT No.: PCT/IB2021/055539
§ 371 (c)(1),
(2) Date: Dec. 21, 2022

(87) PCT Pub. No.: WO2022/003496
PCT Pub. Date: Jan. 6, 2022

(65) Prior Publication Data
US 2023/0165995 A1    Jun. 1, 2023

(30) Foreign Application Priority Data
Jul. 1, 2020    (IT) .................. 102020000015841

(51) Int. Cl.
*A61L 9/18*    (2006.01)
*F24F 8/20*    (2021.01)

(52) U.S. Cl.
CPC ....... *A61L 9/18* (2013.01); *F24F 8/20* (2021.01); *A61L 2209/12* (2013.01); *A61L 2209/16* (2013.01)

(58) Field of Classification Search
None
See application file for complete search history.

(56) References Cited

U.S. PATENT DOCUMENTS 4,115,280 A * 9/1978 Pratt, Jr. ................ A61L 2/08
422/186.1
2013/0248734 A1* 9/2013 Berry .................... A61L 9/18
250/435

FOREIGN PATENT DOCUMENTS

BE     1013093 A5 * 9/2001 ............. A61L 2/08
GB     2340368 A  * 2/2000 ............. A61L 2/084
JP     2000126549 A * 5/2000

OTHER PUBLICATIONS

International Search Report, issued in PCT/IB2021/055539, mailed Oct. 14, 2021, Rijswijk, NL.

* cited by examiner

*Primary Examiner* — Andrew Smyth
(74) *Attorney, Agent, or Firm* — ArentFox Schiff LLP; Michael Fainberg

(57) ABSTRACT

A device for sterilizing air from any bacterium, virus, dust or other organic or non-organic body present in the air of a public or private space, using a sterilization chamber having a laser beam filter is provided. A dense network of laser beams which saturate the sterilization chamber is created. The air forced to go through the sterilization chamber causes every small particle, bacterium and virus of any size to impact on the laser beams, pulverizing, destroying and/or neutralizing itself completely by the large beam energy irradiated for a time ranging from 0.5 to 2 seconds.

16 Claims, 17 Drawing Sheets

Fig. 15
(a)
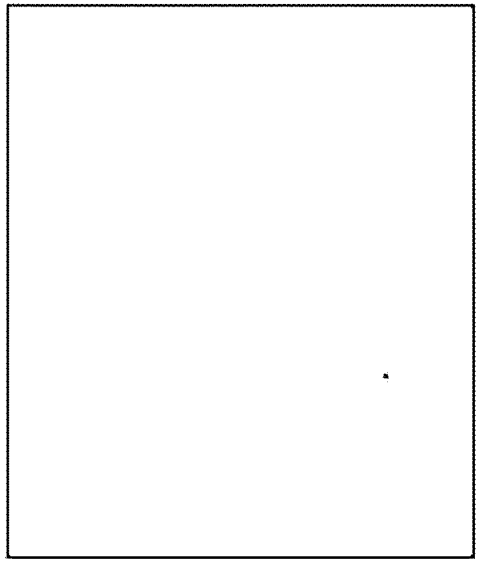
9 mm ⌀
GFP (infected cells)
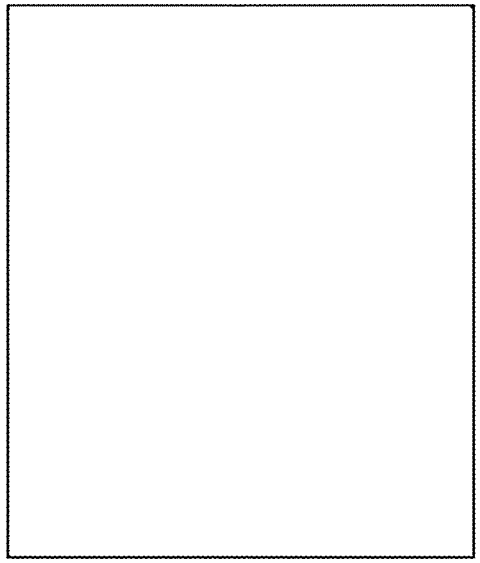
11 mm ⌀
GFP (infected cells)
(b)
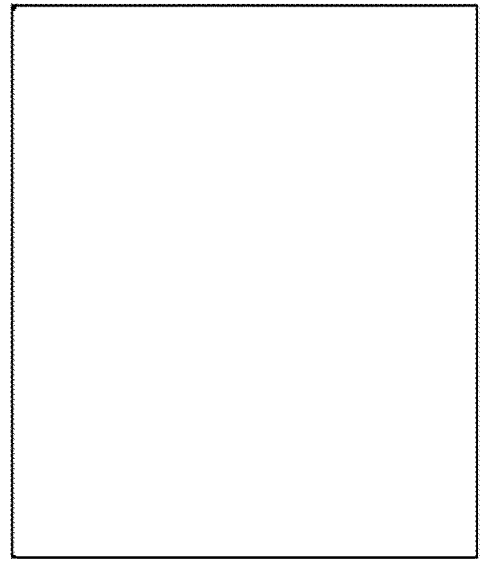
13 mm ⌀
GFP (infected cells)
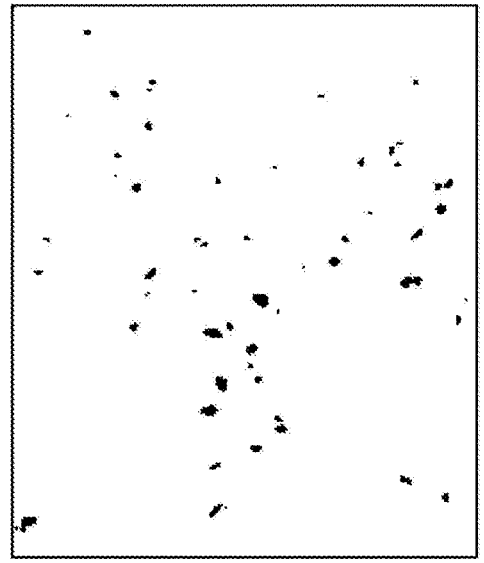
15 mm ⌀
GFP (infected cells)

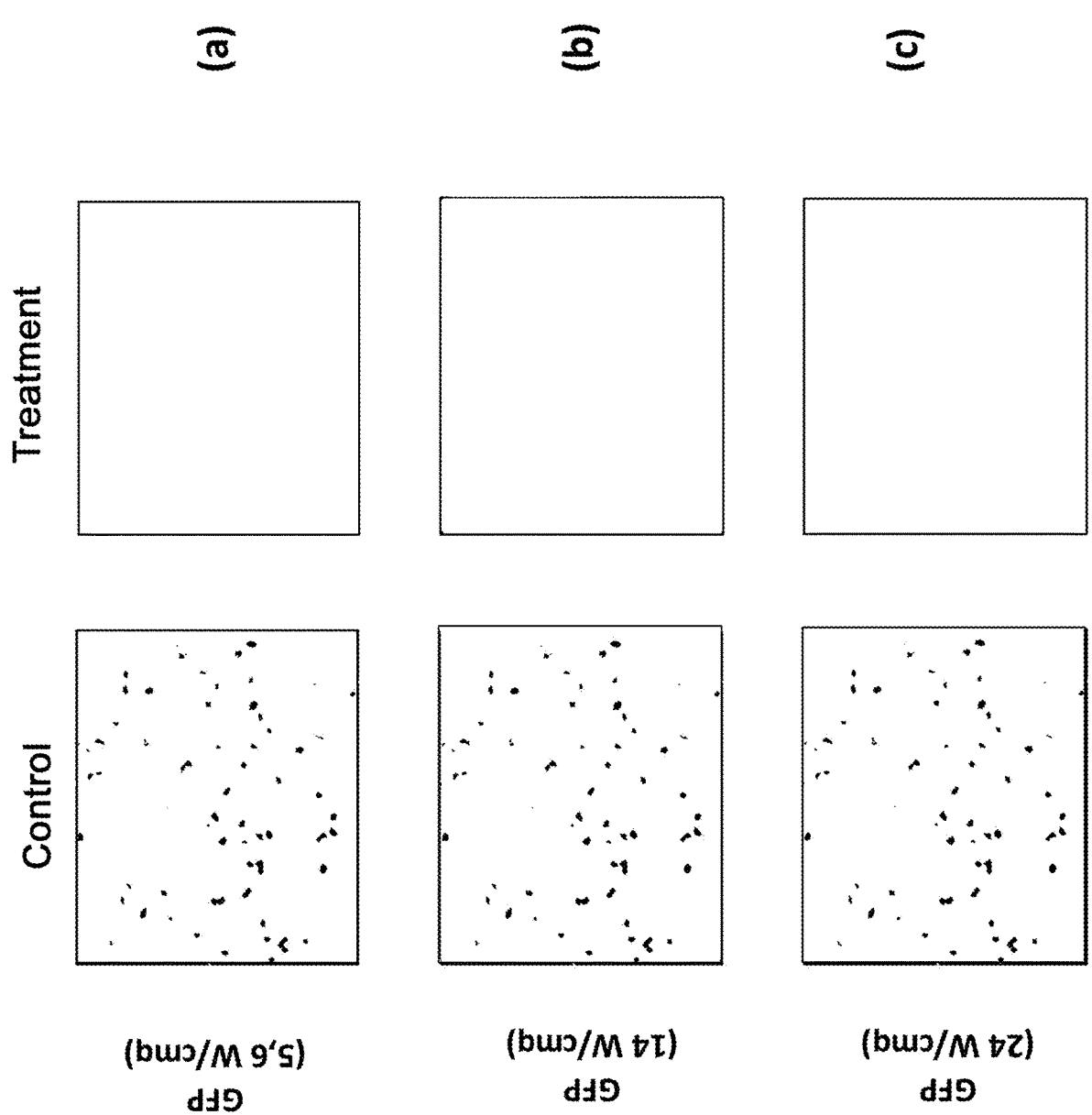

APPARATUS FOR THE STERILIZATION OF AMBIENT AIR BY MEANS OF A LASER RAYS FILTER

CROSS-REFERENCE TO RELATED APPLICATIONS

This application is a National Phase Application of PCT International Application No. PCT/IB2021/055539, having an International Filing Date of Jun. 23, 2021 which claims priority to Italian Application No. 102020000015841 filed Jul. 1, 2020, each of which is hereby incorporated by reference in its entirety.

FIELD OF THE INVENTION

The present invention relates to an apparatus for the sterilization of ambient air by means of a laser beam filter.

In more detail, the present invention relates to an apparatus for the sterilization of air from any bacterium, virus, dust or any other organic or non-organic body present in the air, comprising dangerous insects, of a public or private space, using a sterilization chamber provided with a specific laser beam filter.

BACKGROUND ART

Aerosol in air is one of the fastest means of contagion between people for pathogens such as Covid-19 or other viruses and bacteria.

Contagion mainly occurs when infected people sneeze, cough or speak in areas where people gather or are closely exposed to one another.

The internal circulation of air in closed spaces facilitates the diffusion of these microorganisms in droplets, because they can float in the air and travel at a certain distance due to air recirculation.

In addition to viruses and bacteria which contaminate in an airborne manner, in some regions of the world there are other risk factors associated with small flying insects, in some cases capable of transferring serious pathogens such as malaria.

The current air sterilization devices consist of several systems which use:
- air filtering through EPA or UTRA filters, or other filters of various types and of all kinds; these filters have the problem of the cost of replacing and disposing of the polluting waste formed by the filter itself, moreover the inside of the device remains polluted by viruses or bacteria, contaminating the space during maintenance or inspection;
- aerosol room nebulizers, which saturate the spaces with an alcohol and water-based mist; however, they can only be used in controlled spaces and without the presence of any person in the space to be sterilized, moreover they have a low autonomy due to the refilling of the active disinfectant product;
- electric discharges in air; they have the problem of emitting large quantities of electromagnetic radiation, moreover the relative devices are very heavy (in general several tens of kg), bulky and expensive;
- UVC lamps, for example mercury vapor lamps, with fixed or transportable devices by means of wheels, or by means of motorized systems which move in the space to be sterilized through commands managed by sensors and processors. They can only be used in controlled spaces and without the presence of humans in the room to be sterilized. Furthermore, the UVC-band emission deteriorates the materials present in the spaces, and in particular the plastic material composing the housing of medical devices or many other devices normally present in the spaces.
- UVA and UVB lamps, with fixed or transportable devices by means of wheels, or by means of motorized systems which move in the space to be sterilized through commands managed by sensors and processors. They can only be used in controlled spaces and without the presence of humans in the room to be sterilized.

Other systems simultaneously use one or more of the systems just described. These lamps have the problem that they are very polluting for the space during the disposal step and must be treated as special waste.

Furthermore, systems exist which use a collimated or scanning laser beam by means of complex, moving optical systems. These systems are very delicate and expensive, use dynamic motion systems and poorly stable and expensive laser sources which require frequent, complex, and expensive periodic maintenance.

Other systems convey air through cones or channels so that the air passes through a fixed laser beam. The interior of these systems remains polluted by viruses and bacteria, contaminating the space during maintenance or inspection.

All these systems use either CW lasers or YAG lasers with fast pulses and moving through scanners, but in these cases the irradiance and wavelengths involved do not ensure the air sterilization.

In other systems, wavelengths in the UVA, UVB and UVC range are used, but the very long exposure times (generally greater than 1200 seconds, but also beyond three hours for a more reliable result) and the danger of these ionizing wavelengths for people do not allow their use in the presence thereof, and moreover these wavelengths deteriorate the components made of plastic material, such as gaskets.

Finally, these radiant systems have the limit of dark areas when the spaces are scanned, areas caused by the presence of many objects occupying these spaces, in addition to the fact that in the case of insects, the killing must use electrical systems and the residues must be removed manually. After the life cycle of these lamps, the disposal thereof is polluting for the space and they must be disposed of as special waste.

Even ozone cannot be used in populated spaces, and the same applies to combined ozone-UV lamp systems.

But even if these systems were used in the absence of people, the most dangerous moment for contagion occurs when the spaces are repopulated, because only a minimal probability of contagion exists through contact with surfaces.

Almost all of these systems are not transportable, are bulky or in particular require fixed installations. Furthermore, they cannot be used for other purposes and therefore the installation space cannot be recovered.

Other systems use photocatalysis technology. Titanium dioxide (TiO2) produces a strong oxidative effect in the presence of ultraviolet (UV) light or visible light and therefore can be used as a photocatalytic disinfectant. Although many studies have been reported on the photocatalytic bacteria inactivation, few studies have addressed virus inactivation. This technology is historically used to combat air pollution deriving mainly from the transport field, the industrial field, the activity of power plants and incinerators, from domestic heating, from the use of pesticides in the agricultural field and from dust deriving from the mining field.

The problem with these systems is the disposal of the filter consisting of titanium dioxide and a UV lamp, for example a mercury vapor lamp which emits in the UVC band.

This type of filter must be replaced and disposed of as special waste.

U.S. Pat. No. 4,115,280A describes an apparatus with a chamber for deactivating or activating the biological or chemical activity of macromolecular species, which uses laser radiation at a frequency which excites the vibrational and rotational states of the irradiated species (including viruses and bacteria) and at a sufficient intensity to activate the species (but below the denaturation level) or to a level such that the weak bonds—for example the hydrogen bonds—which determine the spatial character, and therefore the biological activity of the macromolecules, are irreversibly broken to such an extent that the macromolecule loses its original form (the denaturation process) and takes an inactive (denatured) configuration. One of the problems of this apparatus is that the species to be inactivated are substantially on a movable surface and the incidence of the laser beam is not efficient, as the laser is expanded and/or focused and angled as a function of the beam features thereof as well as of the chamber size, and even in this case the actual efficacy on viruses and bacteria is not demonstrated. The apparatus is designed in a complex manner, needs beam absorbers to treat the gases, is expensive and not transportable.

US 2013/248734 describes an air purification apparatus. Energy beams are used which form one or more energy fields inside a chamber to produce an outflow of sterilized air. In order not to deposit contamination residues on the surfaces of the ducts through which the air to be sterilized passes, a load generation system is implemented to repel the particles from the chamber walls, which simply adds to the general principle described by U.S. Pat. No. 4,115,280A and therefore it does not solve the problems already indicated.

JP 2000126549 relates to a system for the decomposition of an exhaust gas from an incinerator or the like, through irradiation with a $CO_2$ laser beam. Since a large number of $CO_2$ molecules is included in the exhaust gas, the $CO_2$ molecules are instantly heated by the $CO_2$ laser beam. A dioxin molecule is adsorbed by the incineration of ash or the like, and when the $CO_2$ molecule is heated, the $CO_2$ molecule collides with the dioxin molecule and the thermal energy owned by the $CO_2$ molecule is transferred to the dioxin molecule so that the dioxin molecule is actually heated and decomposed. No application to viruses or bacteria is described, and beam absorbers are used, leaving all the above problems intact.

There is a need for a laser sterilizer with proven efficacy on viruses and bacteria in gases, which is economical, transportable and possibly does not require beam absorbers and optionally does not require movable surfaces.

PURPOSE AND OBJECT OF THE INVENTION

It is the aim of the present invention to provide a device which solves the problems and overcomes the drawbacks of the prior art.

It is subject-matter of the present invention a device according to the appended claims, which form an integral part of the present description.

BRIEF DESCRIPTION OF THE FIGURES

The invention will now be described by way of example, with particular reference to the drawings of the accompanying figures, in which:

FIG. 15 shows a sixth test like FIG. 14 but with still different irradiances;

FIG. 16 shows a seventh test with laser at 10,600 nm and three different irradiances;

FIG. 20 shows a first embodiment of the device according to the invention using the Venturi effect; and FIG. 21 shows a second embodiment of the device according to the invention using the Venturi effect.

It is worth noting that hereinafter elements of different embodiments may be combined together to provide further embodiments without restrictions respecting the technical concept of the invention, as a person skilled in the art will effortlessly understand from the description.

The present description also refers to the prior art for its implementation, with regard to the detail features which not described, such as, for example, elements of minor importance usually used in the prior art in solutions of the same type.

When an element is introduced it is always understood that there may be "at least one" or "one or more".

When a list of elements or features is given in this description it is understood that the invention according to the invention "comprises" or alternatively "consists of" such elements.

DETAILED DESCRIPTION

According to an aspect of the present invention, an apparatus is provided which incorporates a sterilization chamber in which the ambient air is flowed at a sufficiently low speed by means of a ventilation system, while the chamber is sufficiently filled with a laser beam. Preferably, the air speed can be between 0.01 and 10 m/s (depending on the wavelength used for the laser, the number of laser segments, and the power or irradiance, it is preferably below 3 m/s), so that a given volume of air remains under the action of the laser beam for at least 5 ms, preferably for about 30 ms (in general, the air speed will depend on the number of laser segments between two mirrors, as well as on the wavelength and a predetermined irradiance of the laser beam, as defined below).

Although the present invention always refers to air to be sterilized, the suggested device is also effective for the sterilization of any other non-flammable gas.

Referring to FIG. 1, the apparatus 100 comprises a sterilization chamber 110 and a series of end portions 101. Wheels 106 for transporting the device can be connected on one of the end portions, while the opposite one comprises an opening for the outlet of the sterilized air.

The portions 102 adjacent to the end portions 101 contain the ventilation and/or aspiration system, by means of electronically controlled fans. The lower part 102 (closest to the wheels in the example) may also include a system of ultrasonic proximity sensors and an RGB LED light indicator which indicates the operating states of the invention. The proximity sensors allow to detect the presence or passage of people. Based on this detection, the ventilation system regulates the airflow and the laser power, moving from a low power consumption condition, lowering the laser power and the aspiration flow rate when it does not detect people or the movement of people in the vicinity of the device, to the maximum power of the intake airflow and of the laser power when the sensors detect the presence or passage of people in the vicinity of the device 100. The section indicated by 104 diagrammatically shows the laser optics, the beam expander, which expands the beam (up to a size comparable with or equal to the size—width—of the mirrors 112,113) and reduces the angle thereof to a size for example ≤0.7 mrad (generally less than 1 mrad, preferably between 0.3 and 2 mrad), creating the parallelism which allows the beam to go through tens of meters bouncing between the two mirrors and saturating the laser beam filter chamber. This saturation allows to lower the power of the laser used and thus to reduce the costs of the apparatus.

Section 105 diagrammatically shows the laser beam generator and the power supply thereof.

Other values and provisions are possible respecting the concept of saturation of the sterilization chamber by the laser beam.

According to an aspect of the invention, the sterilization chamber 110 may have a length (height in the figure) between 100 and 1000 cm. According to another aspect of the invention, the sterilization chamber may have a width between 20 and 1000 cm (perpendicular to the vertical in the plane of the sheet). According to a further aspect of the invention, the sterilization chamber may be 2 to 8 cm thick (perpendicular to the sheet, thickness not shown).

Referring also to FIG. 2(*a*), a system of facing mirrors 112, 113 on the two smaller internal walls is installed in the sterilization chamber 110. The mirror system is such as to reflect one or more laser beams carried by the beam expander 104 to the inclined mirror 114 at the edge of one of the two smaller internal walls. The mirror system may be of a material having a coating calibrated on the wavelength of the laser used. FIG. 2 (*b*) shows the same arrangement as that in FIG. 2(*a*) but with incoming air deflection means 116 (see air inlet direction arrow) configured and adapted to convey the airflow into a central volume of the sterilization chamber in the plane between the two mirrored sides, so that the air does not affect these two sides and does not deposit impurities thereon which would reduce the reflective efficiency thereof. Clearly this air deflection will be very efficient at the beginning of the path and less at the end thereof. Other internal or external means for deflecting air to avoid the aforementioned impurities may be provided according to the invention.

The means 116 are particularly effective in avoiding the deposit of material on the mirrors and on the walls of the chamber. These are optional means, and more effective and unexpensive than the loads of patent application US2013/248734.

Referring also to FIG. 3(*a*), the laser beam created by the source and carried by the launch mirror 111 is brought out with an acute angle with respect to the smaller side walls, so as to be reflected by the mirrored walls and go along the sterilization chamber 110 in length. On the same internal side wall a final mirror 114 may be placed which changes the angle of the laser beam 115 to make the laser return back in the opposite direction and possibly to sample the sterilization chamber more closely, as shown in FIG. 3(*b*).

According to an aspect of the invention, after the inlet inclination of the laser, it is also possible to reflect it alternately with a path perpendicular to the advancement direction and again in an inclined manner (with an angle between 0.2 and 1° or between 1 and 15°, not necessarily identical to the inlet angle), so as to thicken the laser network and thus increase the air treatment time (or decrease the laser power). This can be done on the forward path and/or on the return path.

The sampling described is advantageous in that it maximizes the meeting between the air to be purified and the laser beam.

Advantageously, the mirrors can be placed on two opposite sides of the parallelepiped sterilization chamber. In this case, the laser will be positioned so that the laser beam first strikes one of such mirrors with a non-zero angle, at a first end of a smaller side, and is then reflected several times from one smaller side to the other. According to an embodiment of the invention, a mirror with a certain angle is placed at a second end of a smaller side in order to force the laser beam to the opposite path, but with a different inclination angle, so that the entire laser path covers the entire volume.

According to an aspect of the invention, the mentioned laser source may have an average power from 1 to 1000 W CW as a function of the volume of the sterilization chamber, or pulse of any modulation frequency range and duty cycle, but always with an average power from 1 to 1000 W. The wavelength will be specified later in this description. The temperature of the laser source may be kept constant by means of a Peltier or air-cooling system, from the same airflow to be sterilized and/or with a heatsink which may be of aluminum or with a heat pipe. A driver may supply the laser source with constant current or voltage and a photodiode or thermopile system may control the power thereof, preferably constant. According to an aspect of the invention, a thermal sensor monitors and maintains the constant temperature of the laser source, modulating the current to the cooling system.

The laser source may be formed by a single laser beam or by multiple beams which cover all or part of the width of the smaller side inside the parallelepiped-shaped sterilization chamber.

With regard to the inclination of the laser beam(s), they can be inclined by an angle α at the source between 0.2° and 1° or between 1° and 15° (applicable to all embodiments) with respect to a direction perpendicular to the two smaller internal sides. Thereby, the laser beam(s) bounce from mirror to mirror multiple times until they reach the top corner inside the sterilization chamber. These values can also be applied to the return mirror 114 (optional, depending on the beam power needed to destroy the particular virus, it is possible to have multiple return mirrors if there are multiple laser beams), however the inclination β of the latter (i.e., of the beam which bounces back) must be different from the inclination of the beam 115 to the source (features applicable to all embodiments). Thereby, a return "laser network" may be formed by means of the subsequent bouncing between the opposite mirrors, which further completes the "laser beam network" which completely fills the sterilization chamber inside the parallelepiped, creating a laser beam filter which sterilizes the air flowing in the chamber.

Figure 4:
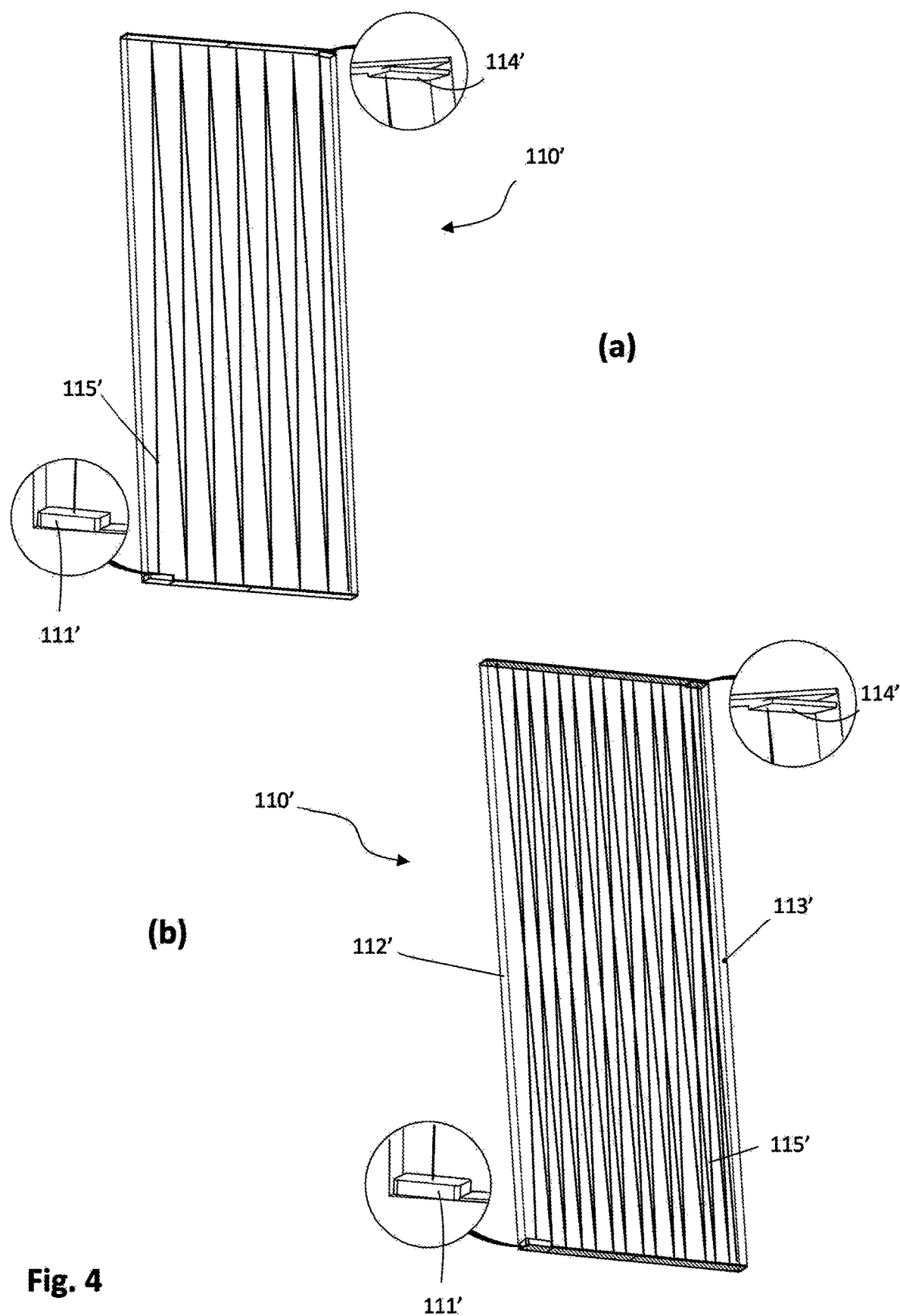
FIG. 4 shows a version of the device in FIG. 3 in which the laser beam goes through the internal space of the device in the longitudinal dimension thereof, with (a) a first angular distribution of a laser beam and (b) a second angular distribution of a laser beam, according to the invention.

Referring to FIG. 4, in device 110' the first mirror 111' which reflects the laser source, the opposite mirrors 112' and 113', the return mirror 114' (optional, depending on the beam power needed to destroy the particular virus) of the beam(s), may also be positioned so as to form the laser beam network 115' with respect to two other opposite smaller sides, without any change in the function of the following invention.

Figure 5:
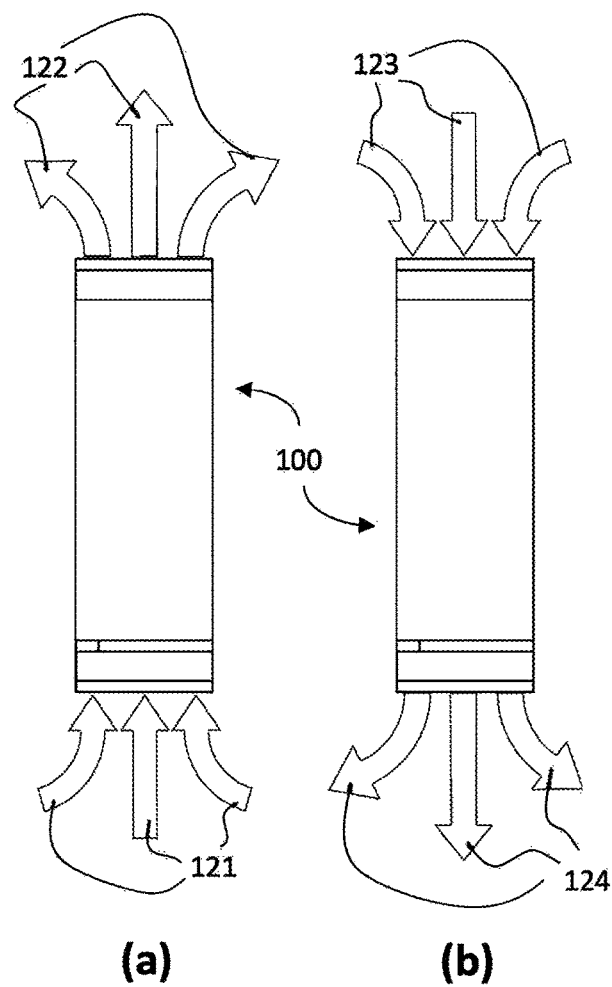
FIG. 5 shows two possible directions (a) and (b) of the airflow to be purified, in a device according to the invention.

The airflow in the device 100 or 110' is better clarified by FIG. 5, in which it can be seen that the air may flow from one smaller side to the other in both directions, i.e. the air can enter in 121 and exit in 122 or enter in 123 and exit in 124.

Optionally, at the two air inlet and outlet ends of the device according to the invention a simple filter is placed (such as the dustproof type) but of a color and a material which does not absorb the wavelength of the laser used, to prevent large bodies (such as any insects or the like) from entering the sterilization chamber. Alternatively, the small-sized insects may be allowed to enter to be destroyed by the laser, as will be seen later in the present description. Furthermore, the inlet and outlet filters may alternatively or additionally have a safety function in the event of device failure, preventing the laser beam(s) from exiting the sterilization chamber, or foreign bodies from entering through the sterilized air outlet.

According to an aspect of the invention, one or more safety sensors are placed in various positions (for example to avoid opening the sterilization chamber while the device is operating), for example at the inlet and outlet of the sterilization chamber. Two switch buttons connected in series may also be provided, which immediately interrupt the laser supply, with interlock function, if the sterilization chamber is opened in some manner (for example a panel is removed which forms the parallelepiped containing the sterilization chamber during an inspection and/or periodic cleaning).

Figure 1:
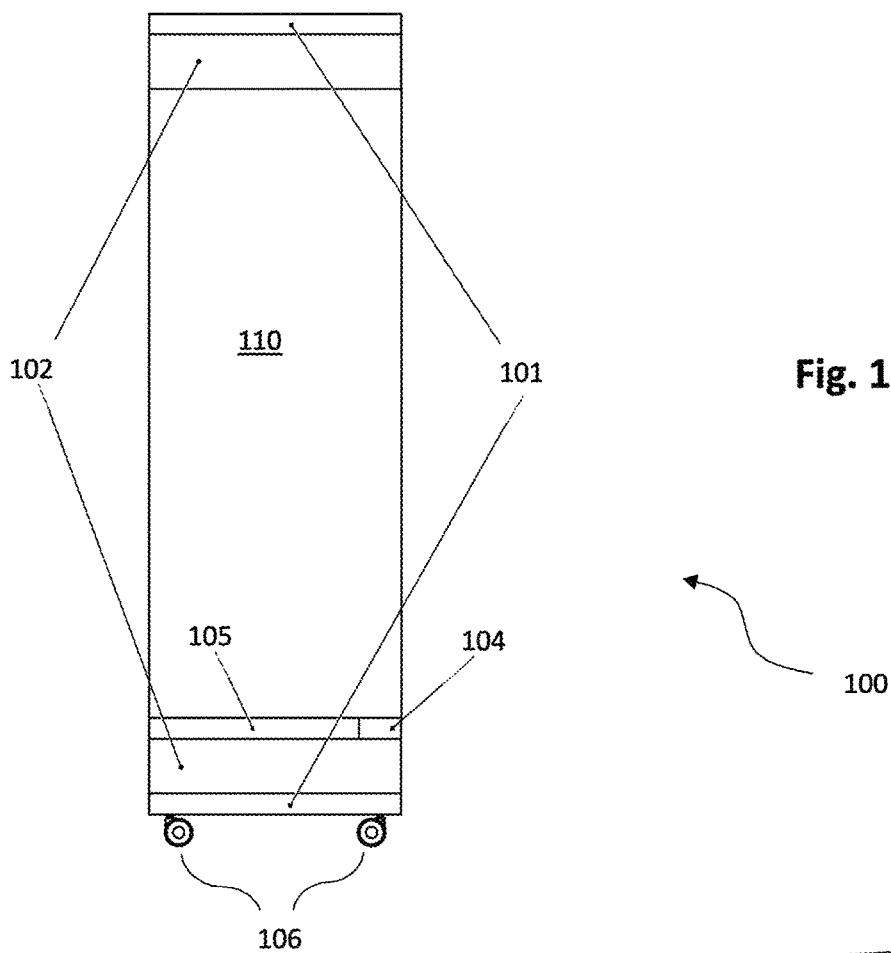
FIG. 1 shows an embodiment of the device according to the invention in a transportable version with wheels, in a vertical position.
Figure 2:
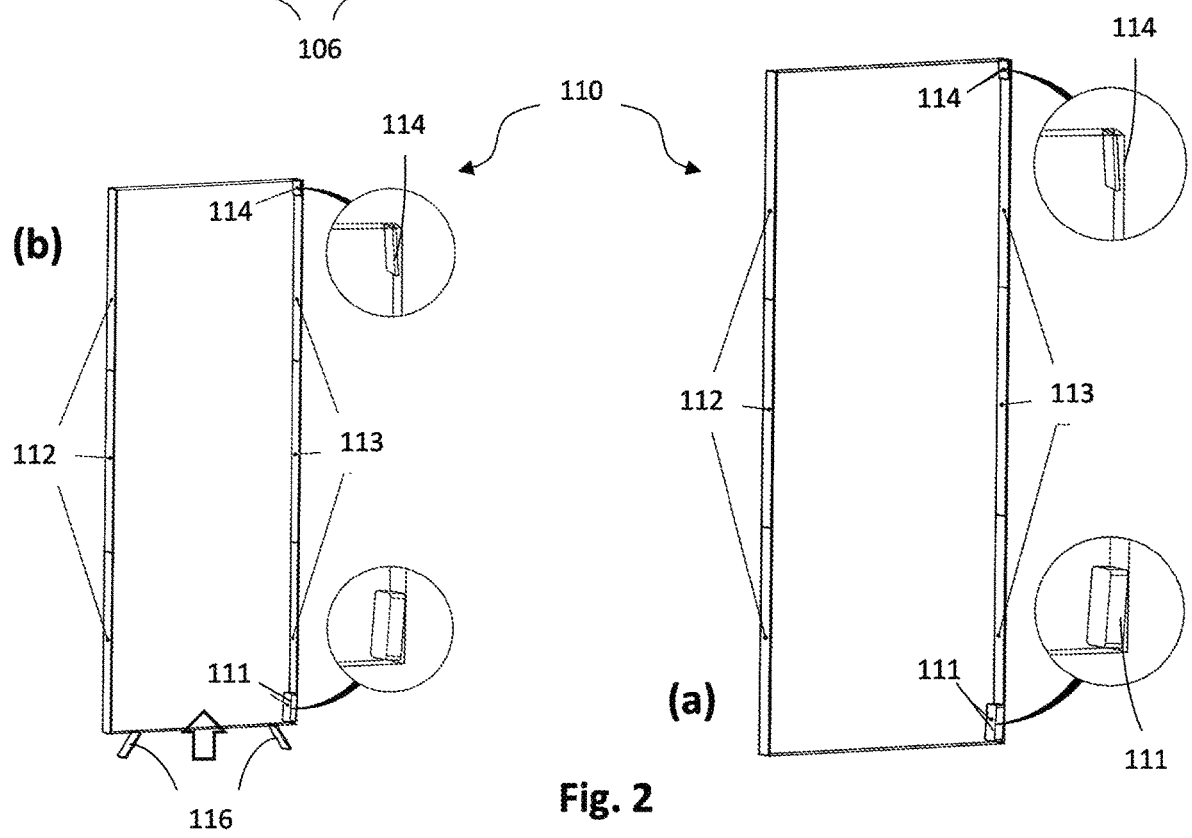
FIG. 2 shows in (a) an internal view of a main portion of the device in FIG. 1, and in (b) a variant with incoming air deflection means.
Figure 3:
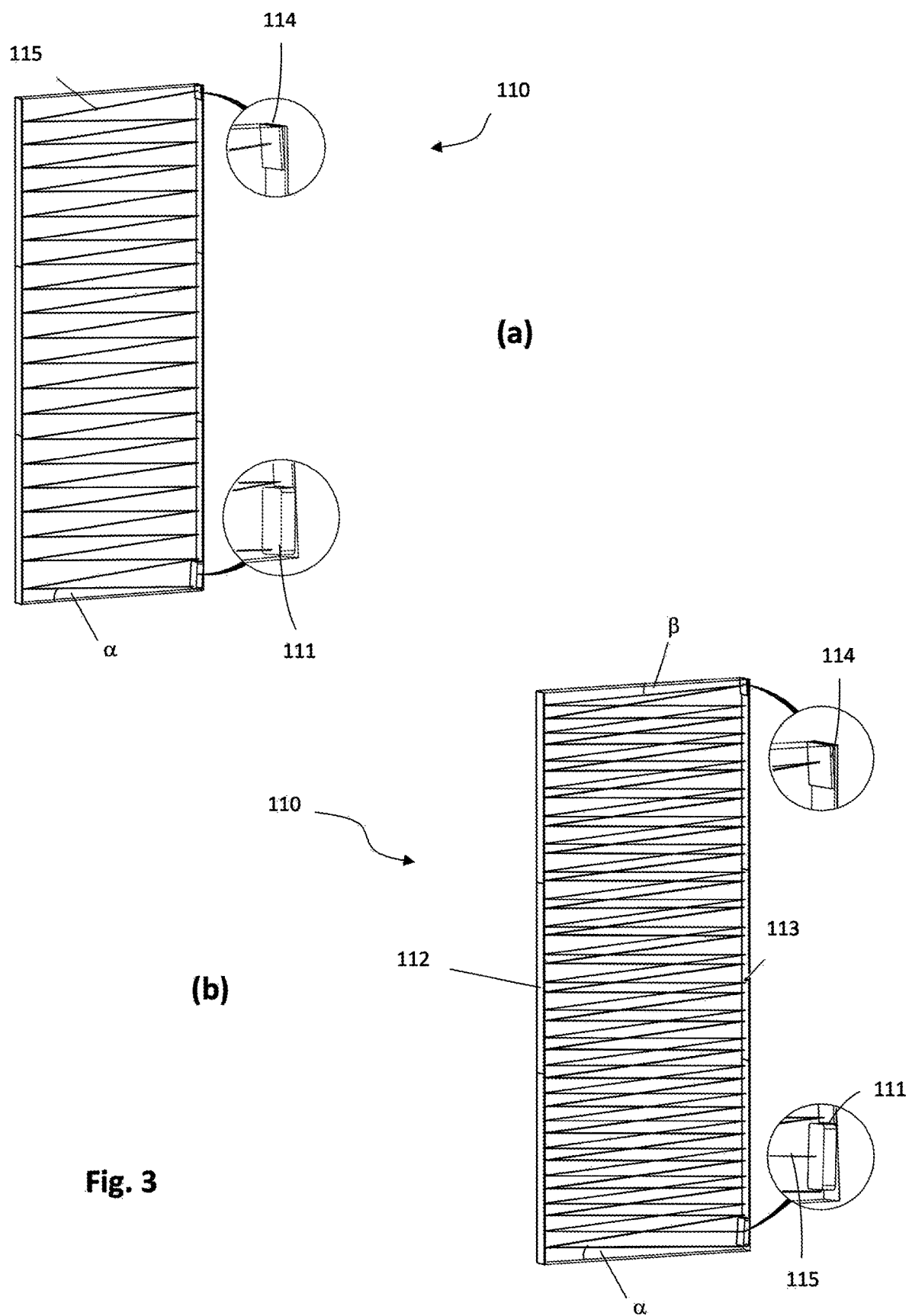
FIG. 3 shows the view in FIG. 2 with (a) a first angular distribution of a laser beam and (b) a second angular distribution of a laser beam, according to the invention.

When the invention is in the form of a parallelepiped, it may be fixed to a wall in a vertical or horizontal position, to a ceiling in a longitudinal or transverse position, or hung from a ceiling, horizontally or vertically by means of metal cables or other means. The device may be provided with wheels (see FIG. 1) and be positioned horizontally or vertically, and this allows to position it anywhere in a room.

Figure 6:
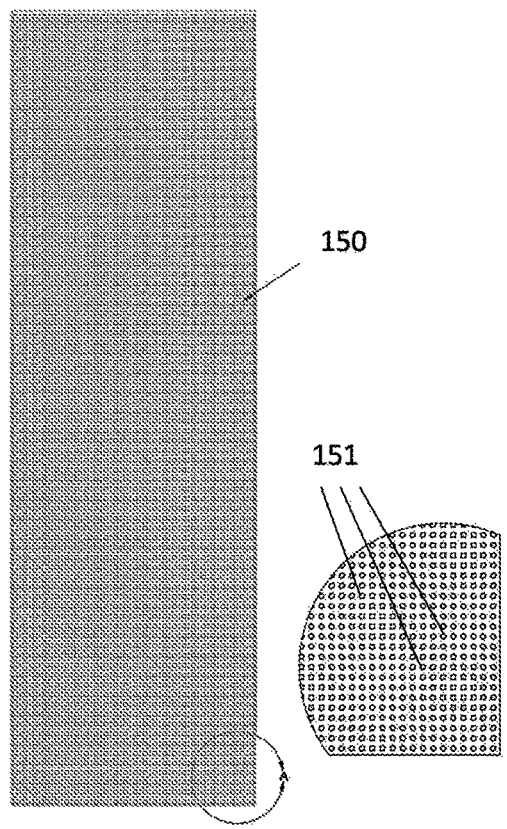
FIG. 6 shows an embodiment of an air collection grid, according to an embodiment of the invention.
Figure 7:
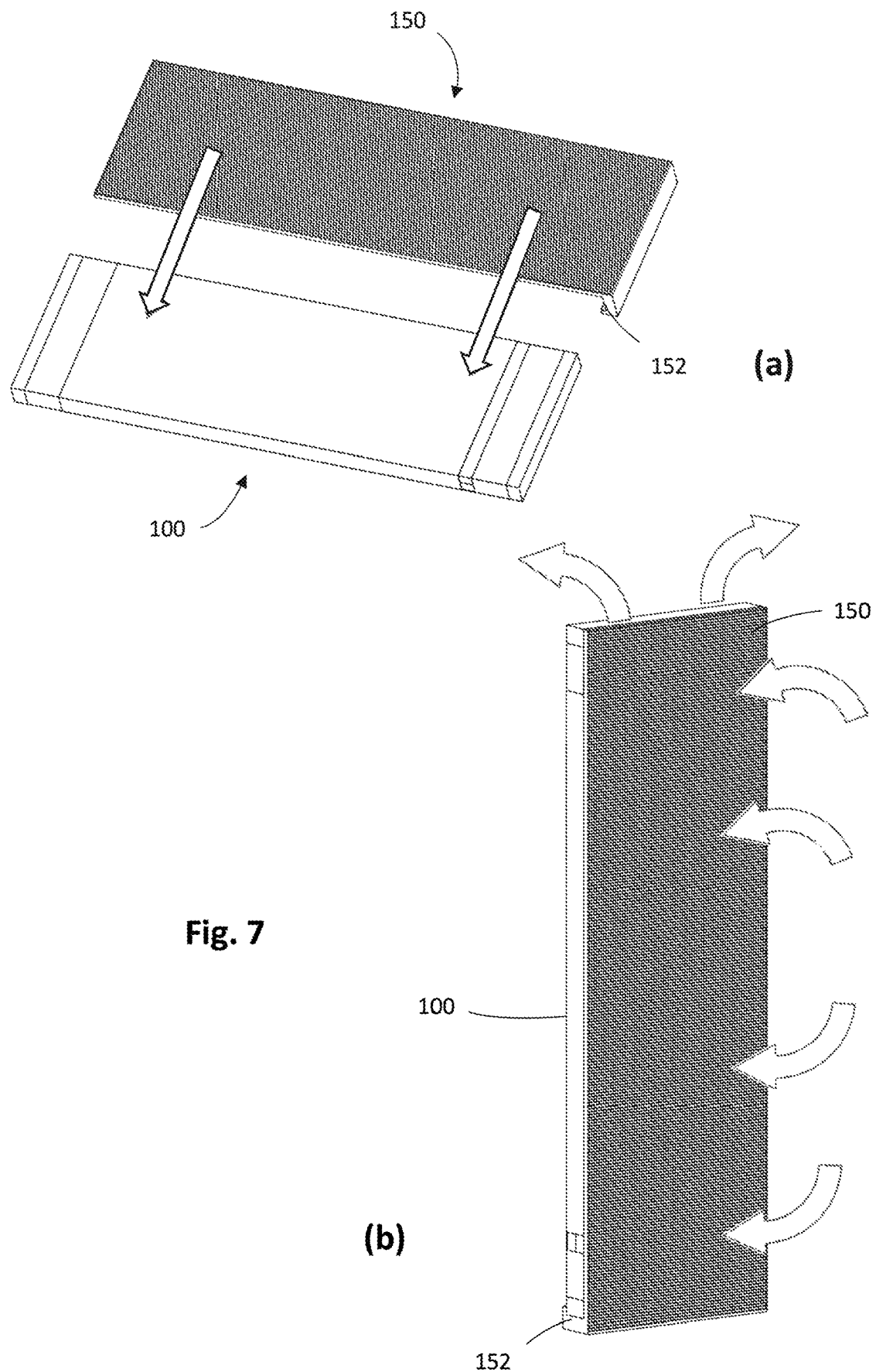
FIG. 7 shows in (a) an assembly example of the grid in FIG. 6 and in (b) some airflows with the grid assembled.

Referring to FIGS. 6 and 7, in a specific embodiment of the invention, the device has external panels (in general "gas collectors" placed on a wall portion outside the sterilization chamber) which also form the device housing 150 at least in part (e.g., removable), which may also be used as a space for multiple functions, including:

advertising services;
general and emergency notices;
graphics or artistic paintings;
support for fixing LCD or OLED or any other active computer screen or entertainment screen;
incorporation of speakers or mono or stereo sound system.

Such panels 150 may for example be of any metal or plastic material.

The panels 150 may have a multiplicity of holes 151 of the same or different size for a homogeneous aspiration in the whole surface of the panels and serve as air collectors. In this case, it is convenient that there is an end 152 which connects to the air inlet in the device 100.

The device according to the invention may be conveniently powered in alternating voltage from 100 to 240V AC from 50 to 60 Hz, or in DC from 12 to 48 Vdc by means of special power supply means.

Figure 8:
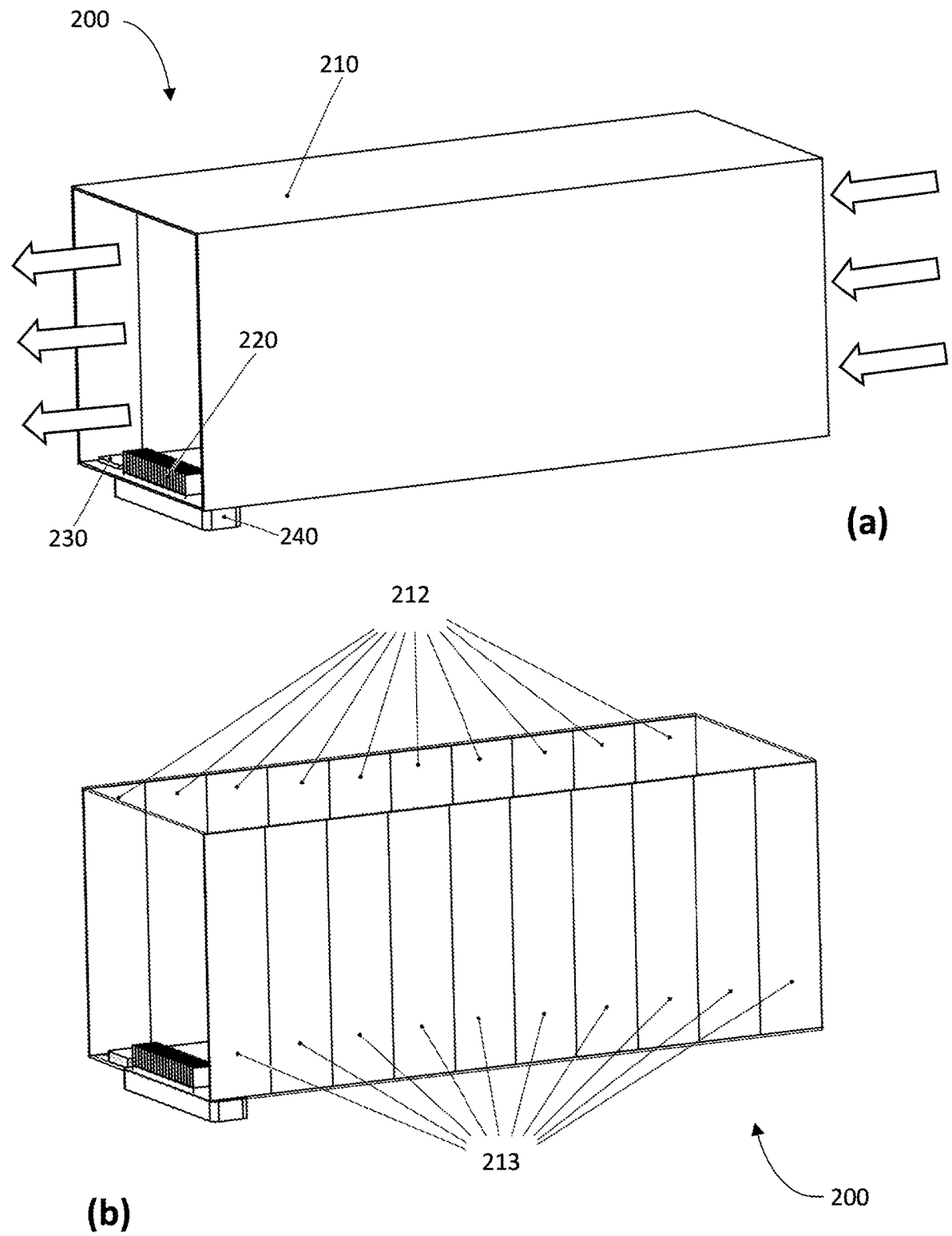
FIG. 8 shows a further embodiment of the device according to the invention adapted to be installed in line with ventilation ducts, with in (a) the indication of the airflow (arrows) and in (b) the indication of the mirrored modules.
Figure 9:
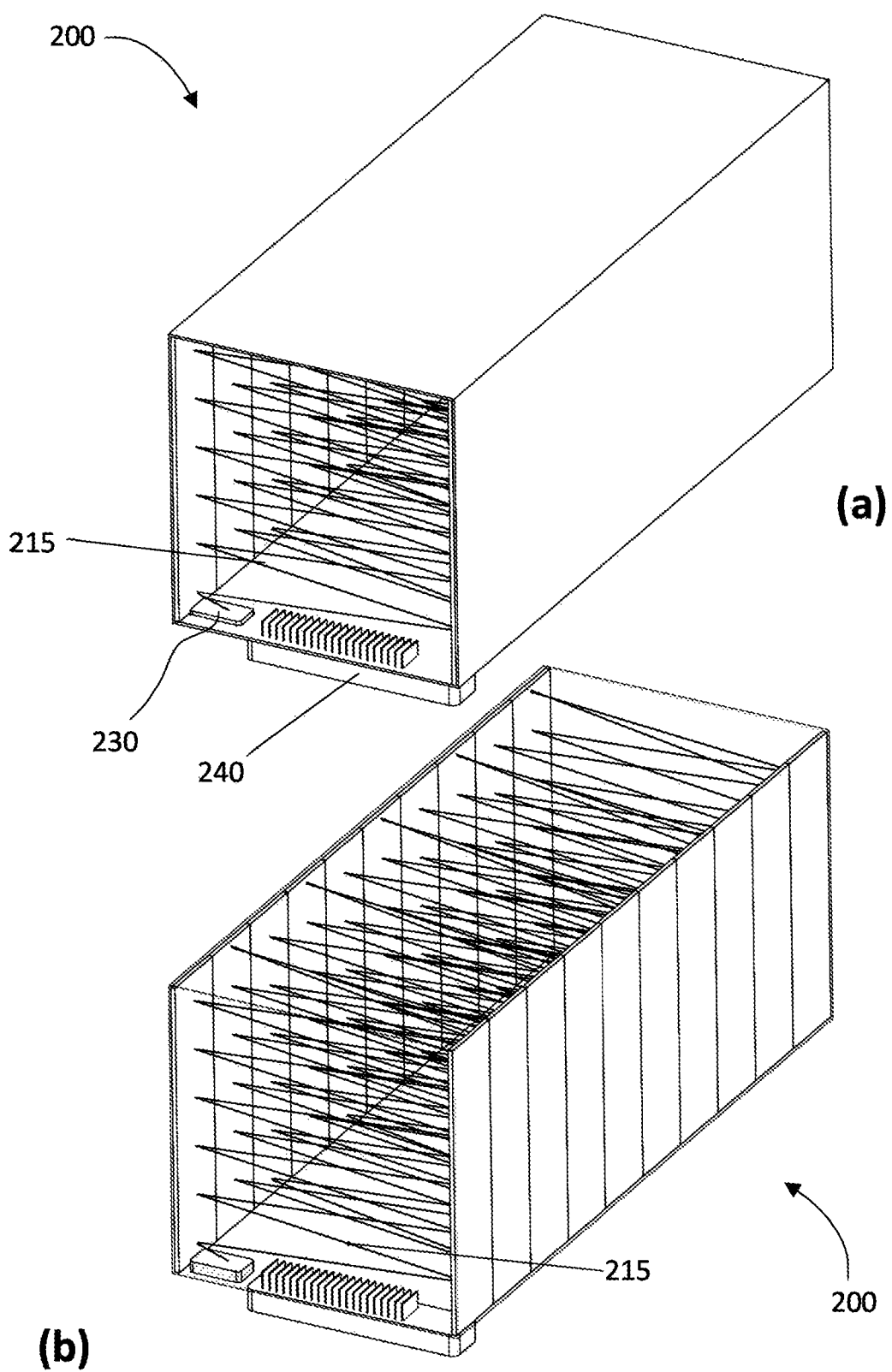
FIG. 9 shows a perspective view from above of the device in FIG. 8 with the upper wall removed, in which in (a) a first distribution is shown and in (b) a second distribution of laser beams is shown, according to an embodiment of the invention.

Referring now to FIG. 8, in a different embodiment, the sterilization device 200 has a shape and an arrangement adapted for use in the ventilation ducts of apartments and offices. It is usually a rectangular tube 210 in which air enters at one end and then exits sterilized at the opposite end. Two opposite walls comprise, along the airflow direction, two opposite sets of internal mirrors 212, 213 between which a laser beam 215 (produced by laser system 220) bounces as in the previous embodiments, generated by the laser source 240 and exiting from the outlet 230. A return mirror is also present as in the previous embodiments (not shown in the figures).

Although in the previous embodiments a device with a parallelepiped-shaped sterilization chamber has been illustrated, any other useful form which allows the creation of a laser beam network is possible. For example, according to the invention it is possible to obtain the device in the form of a cylinder, where the mirrors are inside on the two circular bases, and the laser beams go through the height of the cylinder with inclination angles like in the other embodiments, where however the angle varies in the two directions of the base, or there are multiple laser sources emitting from one of the two bases or from both (the latter feature also being possible in the other embodiments).

Examples of Sterilization with the Device According to the Invention

Example No. 1

The sterilization functionality is explained here according to an example mathematical model. Although the calculation has general value, reference will be made to a specific example in which the sterilization chamber is in the form of a parallelepiped.

Therefore, a parallelepiped is considered with dimensions of length H width W and thickness T. For example, these dimensions may be:

$H=1.5$ m $W=0.6$ m $T=0.04$ m

The airflow flows along the length H of the parallelepiped at a speed v, going through the section S of the parallelepiped $S=W \cdot T$ A certain airflow rate Q to be sterilized by means of laser radiation inside the parallelepiped is considered.

The air speed inside the parallelepiped must therefore not exceed $V_{max}$ $V \leq V_{max} = Q/S$ The exposure time t of the air to the laser radiation must be greater than $T_{min}$:

$T \geq T_{min} = H/V$

With the example values above, we obtain:

$H=1.5$ m $W=0.6$ m $T=0.04$ m $S=W \cdot T=0.6 \cdot 0.04=0.024$ m$^2$ $Q=120$ m$^3$/h$=0.033$ m$^3$/s $V \leq V_{max} = Q \div S = 0.0333/0.024 = 1.39$ m/s $t \geq t_{min} = H/V = 1.5/1.39 = 1.08$ s The result of this first example shows how the air, in this sterilization chamber, is exposed to the laser beam filter radiation for 1.08 s by going through the laser beam filter at a speed of only 1.39 m/s with a filtered airflow of 120 m$^3$/h.

It should be noted here that the laser manages to fill (sample) the entire sterilization chamber due to the particular positioning of the example of the parallelepiped. In fact, being just 4 cm thick, a laser with a beam width of the same radius is sufficient to ensure sterilization.

As for the angles α and β, they can be chosen in this example between 1 and 5° so that the device is particularly optimized in efficacy. This interval is also valid for the following examples where more reflections or more beams have been used. Under the degree of inclination it is possible and particularly effective in all embodiments in which it is convenient to multiply the reflections of the laser beam, for example when the laser beam enters a small central opening in a wall of the device and is reflected both on the right and on the left and the air exits from both sides, this being a different embodiment from those shown in the figures. Therefore, an optimal range between 0.2 and 5 degrees can also be chosen for the angles α and β in each embodiment.

As for the laser power, the following can be had as an example:

Laser source power=3 W

Irradiance$(E)=30$ KW/m$^2$

Exposure time$(t)=1.08$ s

Radiant exposure $E*t=32,400$ J/m$^2$

Example No. 2

A parallelepiped is therefore still considered with dimensions of length H width W and thickness T. For example, these dimensions may always be:

$H=1.5$ m $W=0.6$ m $T=0.04$ m

The airflow flows along the length H of the parallelepiped at a speed v, going through the section S of the parallelepiped $S=W \cdot T$ A certain airflow rate Q to be sterilized by means of laser radiation inside the parallelepiped is considered. The air speed inside the parallelepiped must therefore not exceed $V_{max}$ $V \leq V = Q/S$ The exposure time t of the air to the laser radiation must be greater than $T_{min}$:

$T \geq T_{min} = H/V$

With the example values above, we obtain:

$H=1.5$ m $W=0.6$ m $T=0.04$ m $S=W \cdot T=0.6 \cdot 0.04=0.024$ m$^2$ $Q=240$ m$^3$/h$=0.066$ m$^3$/s $V \leq V_{max} = Q \div S = 0.0666/0.024 = 2.77$ m/s $t \geq t_{min} = H/V = 1.5/2.77 = 0.54$ s The result of this second example shows how the air, in this sterilization chamber, is exposed to the laser beam filter radiation for only 0.54 s compared to example No. 1, going through the laser beam filter at a speed of only 2.77 m/s with a filtered airflow of an impressive 240 m$^3$/h.

This is possible by doubling the number of laser beams going through the filter chamber, through a return laser beam which extends in a volume parallel to the forward beam, thus being able to double the thickness of the sterilization chamber (or halve the section of the beam). Using the same concept, the parallel volumes may also be more than two.

Furthermore, it is possible to position other return mirrors at the bottom and at the top with respect to the airflow direction, so as to bounce the laser beam several times at different angles to create an even denser network of laser irradiation segments.

As far as laser power is concerned, it may remain the same, for example:

Laser source power always=3 W

Irradiance$(E)$=30 KW/m$^2$

Exposure time$(t)$=1.08 s

The radiant exposure will be double as the number of beams inside the filter chamber have doubled, but with a double airflow compared to example No. 1, in fact the radiant exposure will still remain E*t=32,400 J/m$^2$.

Example No. 3

A parallelepiped is therefore still considered with dimensions of length H width W and thickness T. For example, these dimensions may be:

$H$=1.5 m $W$=0.6 m $T$=0.04 m

The airflow flows along the length H of the parallelepiped at a speed v, going through the section S of the parallelepiped $S=W \cdot T$ A certain airflow rate Q to be sterilized by means of laser radiation inside the parallelepiped is considered. The air speed inside the parallelepiped must therefore not exceed $V_{max}$ $V \leq V = Q/S$ The exposure time t of the air to the laser radiation must be greater than $T_{min}$:

$T \geq T_{min} = H/V$

With the example values above, we obtain:

$H$=1.5 m $W$=0.6 m $T$=0.04 m $S=W \cdot T=0.6 \cdot 0.04=0.024$ m$^2$ $Q$=240 m$^3$/h=0.066 m$^3$/s $V \leq V_{max} = Q \div S = 0.0666/0.024 = 2.77$ m/s $t \geq t_{min} = H/V = 1.5/2.77 = 0.54$ s The result of this third example shows how the air, in this sterilization chamber, is exposed to the laser beam filter radiation for only 0.54 s, going through the laser beam filter at a speed of only 2.77 m/s with a double filtered airflow of 240 m$^3$/h compared to example No. 1.

This is possible by doubling the laser source power, as described in the example:

Laser source power=6 W

Irradiance$(E)$=60 KW/m$^2$

Exposure time$(t)$=0.54 s

The radiant exposure will always be the same, but with a double airflow with respect to example No. 1, in fact radiant exposure will still remain E*t=32,400 J/m$^2$.

Example No. 4

A parallelepiped is therefore still considered with dimensions of length H width W and thickness T. For example, these dimensions may be:

$H$=1.5 m $W$=0.6 m $T$=0.04 m

The airflow flows along the length H of the parallelepiped at a speed v, going through the section S of the parallelepiped $S=W \cdot T$ A certain airflow rate Q to be sterilized by means of laser radiation inside the parallelepiped is considered. The air speed inside the parallelepiped must therefore not exceed $V_{max}$ $V \leq V = Q/S$ The exposure time t of the air to the laser radiation must be greater than $T_{min}$:

$T \geq T_{min} = H/V$

With the example values above, we obtain:

$H$=1.5 m $W$=0.6 m $T$=0.04 m $S=W \cdot T=0.6 \cdot 0.04=0.024$ m$^2$ $Q$=240 m$^3$/h=0.066 m$^3$/s $V \leq V_{max} = Q \div S = 0.0666/0.024 = 2.77$ m/s $t \geq t_{min} = H/V = 1.5/2.77 = 0.54$ s The result of this fourth example shows how the air, in this sterilization chamber, is exposed to the laser beam filter radiation for only 0.54 s, going through the laser beam filter at a speed of only 2.77 m/s with a double filtered airflow of 240 m$^3$/h compared to example No. 1.

This is possible by using a wavelength which has a much higher water absorption index than other wavelengths and by adjusting the laser source power, as described in the example:

Laser source power=5.6 W

Irradiance$(E)$=56 KW/m$^2$

Exposure time$(t)$=0.54 s

Absorption index>5 times that at 1940 nm wavelength

The radiant exposure will be slightly lower, but the absorption index is much higher than the wavelength at 1940 nm, and with a double airflow compared to Example No. 1, the same results will be obtained if not amplified, leaving room for an even higher increase in airflow. In detail, the radiant exposure here is equal to E*t=30,240 J/m² but with an efficiency of this radiant exposure at 10600 nm>5 times that at 1940 nm.

It is possible to calculate the airflow speed along shapes other than that of the parallelepiped with the same principles, therefore as a function of the number of laser segments, the laser wavelength and irradiance.

Usable Wavelengths

The validity and efficacy of the laser in the destruction of viruses and bacteria, as well as of infection-carrying insects, has been independently assessed by the ICGEB (Centro internazionale di ingegneria genetica e biotecnologie) based in Trieste, Italy. ICGEB is an autonomous intergovernmental organization which operates within the United Nations system and manages 46 state-of-the-art laboratories in different parts of the world.

The optimal wavelengths and irradiances capable of killing viruses emerged from this assessment, as follows: 1940 nm (semiconductor laser or Thulium fiber laser), 2950 nm (Erbium Yag Laser), 9300 nm, 10600 ($CO_2$ laser), with a 15% variation around these values which turn out to be laser absorption peaks by the water. Although other values outside these ranges are also possible, the efficiency of the lasers in these cases would be too low (less than 1%) to be used effectively and conveniently.

As for the 9,300 nm wavelength, it is usable but has two disadvantages:
 efficiency lower than 10600 nm (6-7% against the 10% of 10600 nm);
 water absorption less than 10600 nm.

These wavelengths result in the destruction of viruses and bacteria by photomechanical and photothermal effect. The use of a photochemical effect would require excessively long radiation times, which would not allow to obtain a functional result of this laser beam filter, even at very high irradiances over 150 W/cm2.

Demonstration Tests

Below are some demonstration tests for the wavelengths between blue and infrared. Other similar tests have been carried out up to wavelengths above 12,000 nm, of which only one is reported at 10,600 nm. Although the viruses used are HEK 293T and AAV lentiviral vector, other viruses such as coronavirus have similar structures and dimensions and therefore the device according to the present invention will be effective because it acts on the destruction by local temperature rise (photothermal and photomechanical effects) and not on some photochemical effect.

Test No. 1—Test with 445 nm Blue Laser

Figure 10:
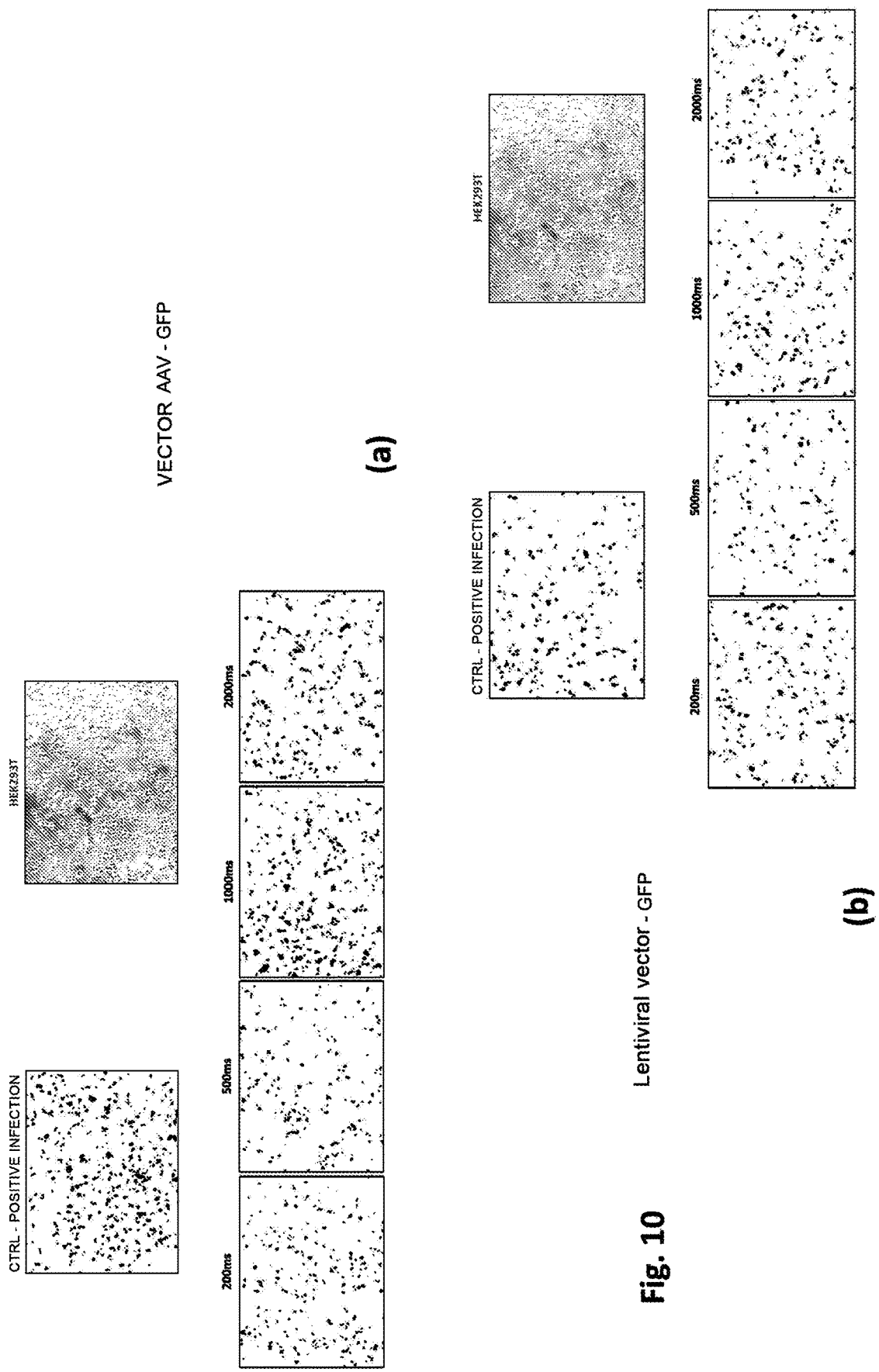
FIG. 10 shows a first virus destruction test with 445 nm Blue Laser.

As can be seen from FIG. 10, using a HEK 293T cell line; 50k per well; 24 wells (100 µl, 200 mm² surface), with two different viruses:
 (a) Vector AAV—GFP;
 (b) Lentiviral vector—GFP;
 the Blue Laser at 445 nm, even with an irradiance of 4 W/cm², energy 1.6-18 J, precisely 1.6 J, 4 J, 8 J, 18 J at the respective times 200, 500, 1000, 2000 msec, did not give any results.

Test No. 2—Further 445 nm Blue Laser Test

The test was carried out with the same HEK293T cell line but with different cell amounts and irradiations for a time from 1 to 4 seconds:
 HEK293T; 50k for 6 wp (5k cells/cm²), 1.2 W/cm² irradiance
 HEK293T; 5K for 96 wp (15k cells/cm²), 8 W/cm² irradiance
and with a single virus AAV vector—GFP, 6 and 96 wells (10 µL virus in PBS).

The blue laser was used with powers 8 J; 24 J; 32 J corresponding to 1, 3, 4 pulses, respectively.

Figure 11:
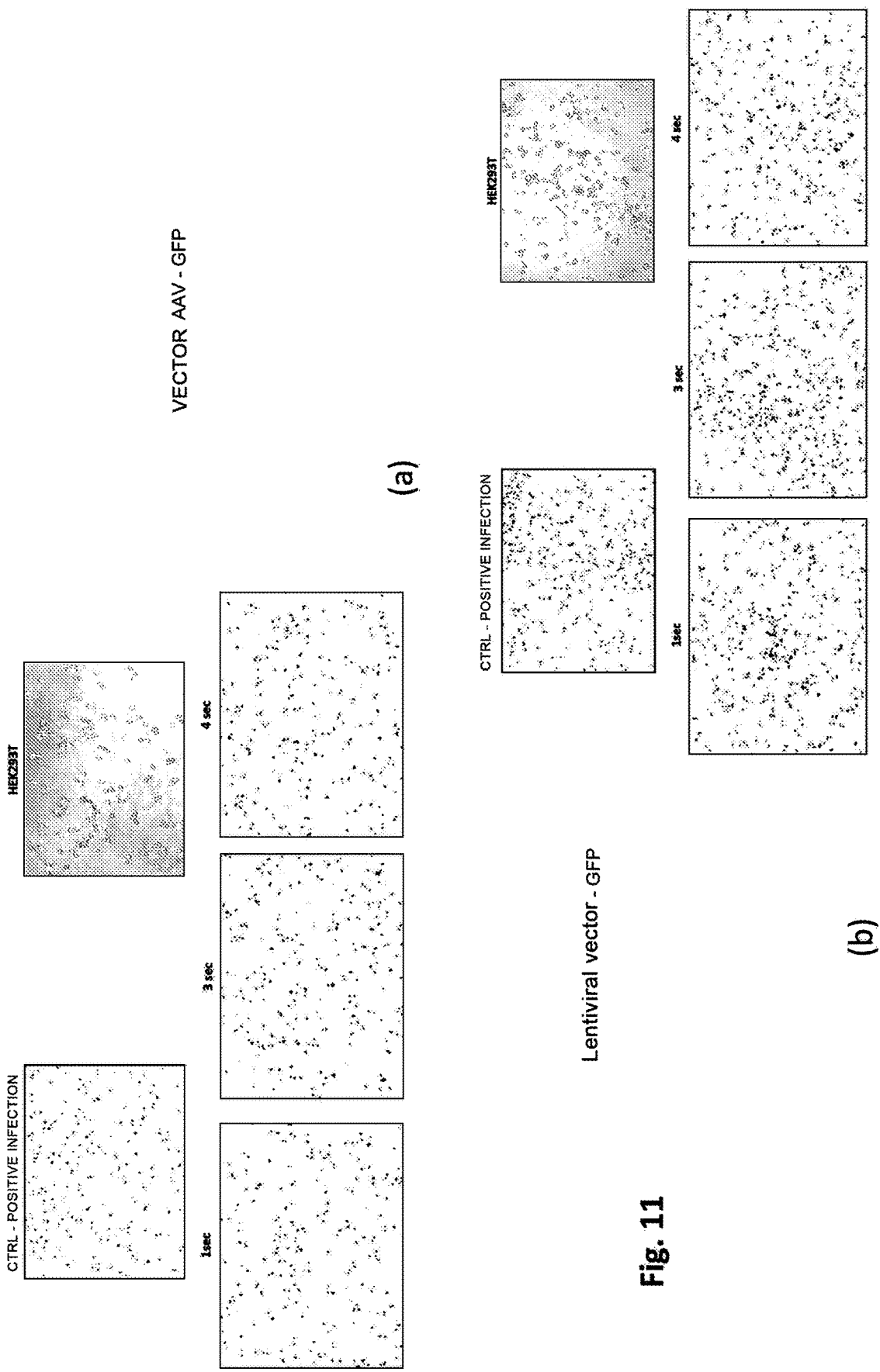
FIG. 11 shows a second virus destruction test with 445 nm Blue Laser but with different irradiances.

Referring to FIG. 11, as can be seen with the AAV virus with (a) 6 and (b) 96 wells, the Blue Laser at 445 nm, albeit with an irradiance increased to 8 W/cm², and the energy increased up to 32 J, did not yet give any results.

Test No. 3—Test with IR Laser

The wavelength used was 1940 nm, with an $H_2O$ absorption factor corresponding to 99.3%.

The laser power was 2.4 W, used with two irradiance values of 0.35 W/cm² and 3 W/cm² for two seconds of exposure.

The viruses used were:
 HEK293T; 50k for 6 wp (5k cells/cm²)–5 drops of virus (1 µL each);
 HEK293T; 5K for 96 wp (15k cells/cm²)–1 drop of virus (1 uL);
 AAV vector—GFP, in 6 and 96 wells (drops of 1 µL).

Figure 12:
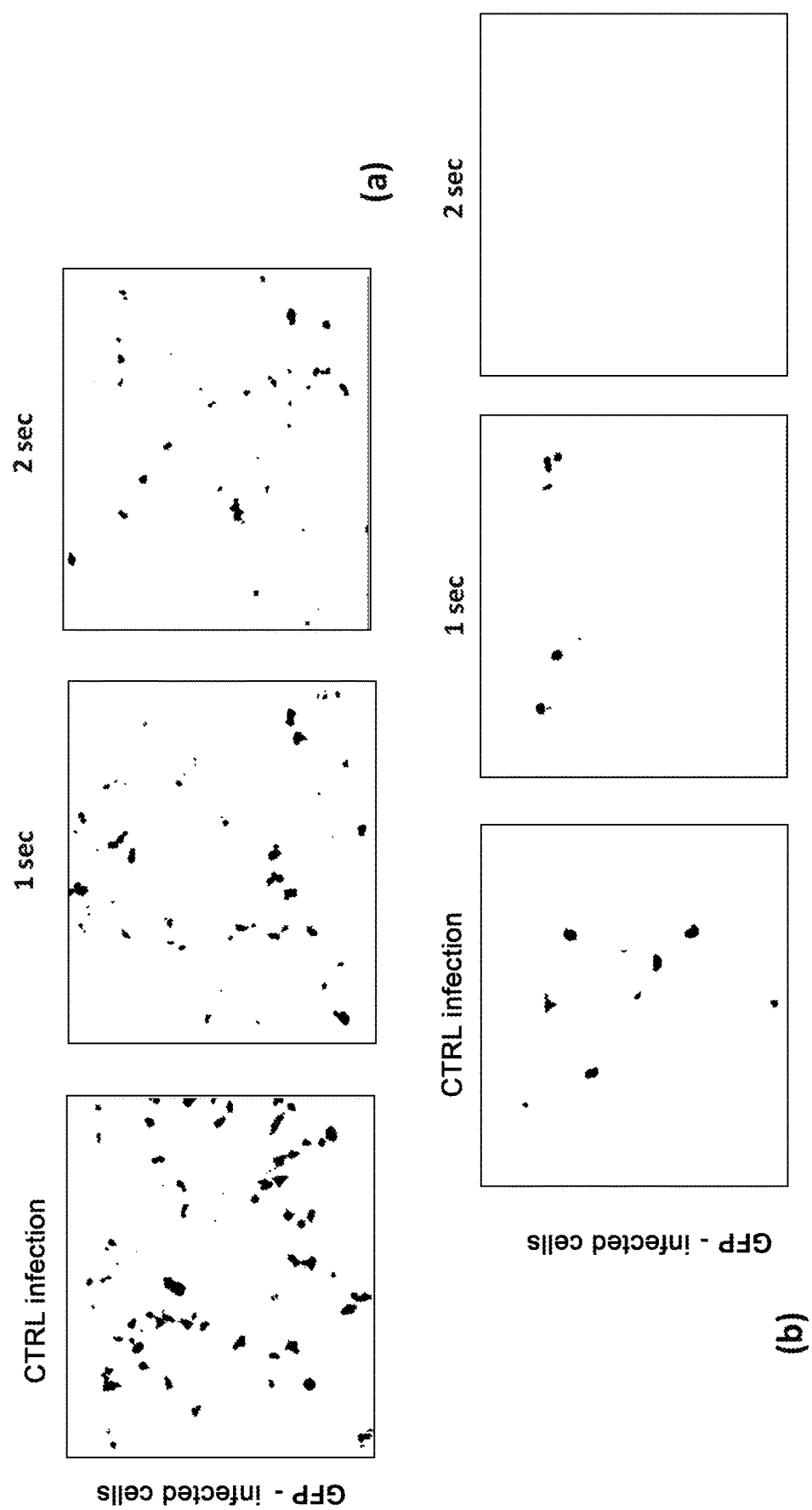
FIG. 12 shows a third virus destruction test with 1940 nm IR Laser.

Referring to FIG. 12, which reports the results only for the AAV virus, with the irradiance of 0.35 W/cm² in (a) a decrease in viral activity was obtained, while complete destruction of the virus with an irradiance of 3 Wcm² in (b) was obtained.

Test No. 4: Comparison of the Sterilizing Effect Between 3 Different Wavelengths, at High Irradiance: 445 nm; 970 nm; 1980 nm The three wavelengths referred to in the previous tests were tested, but with greater irradiances and exposure time of 1 and 2 seconds (in focus), or 1+1 and 2+2 seconds (in and out of focus: in the first exposure time of 1 and 2 seconds, the laser is focused on the virus drop (in focus), and subsequently a second pulse of 1 and 2 seconds radiates the entire surface of the Eppendorf tubes (out of focus) to avoid the viruses remaining attached to the walls). The wavelengths and irradiances are as follows:
 wavelength 445 nm—irradiance 8 KW/cm²
 wavelength 970 nm—Irradiance 15 KW/cm²
 wavelength 1940 nm—Irradiance 2.5 KW/cm²

The viruses used were:
 HEK293T; 5K for 96 wells (15k cells/cm²)-1 drop of virus (1 µL) in Eppendorf tube;
 AAV vector—GFP
 Lentiviral vector—GFP (concentration: 1× and 10× preparation)

AAVs and lentiviruses were added in 1.5 mL Eppendorf tube (drop of 1 µL).

Figure 13:
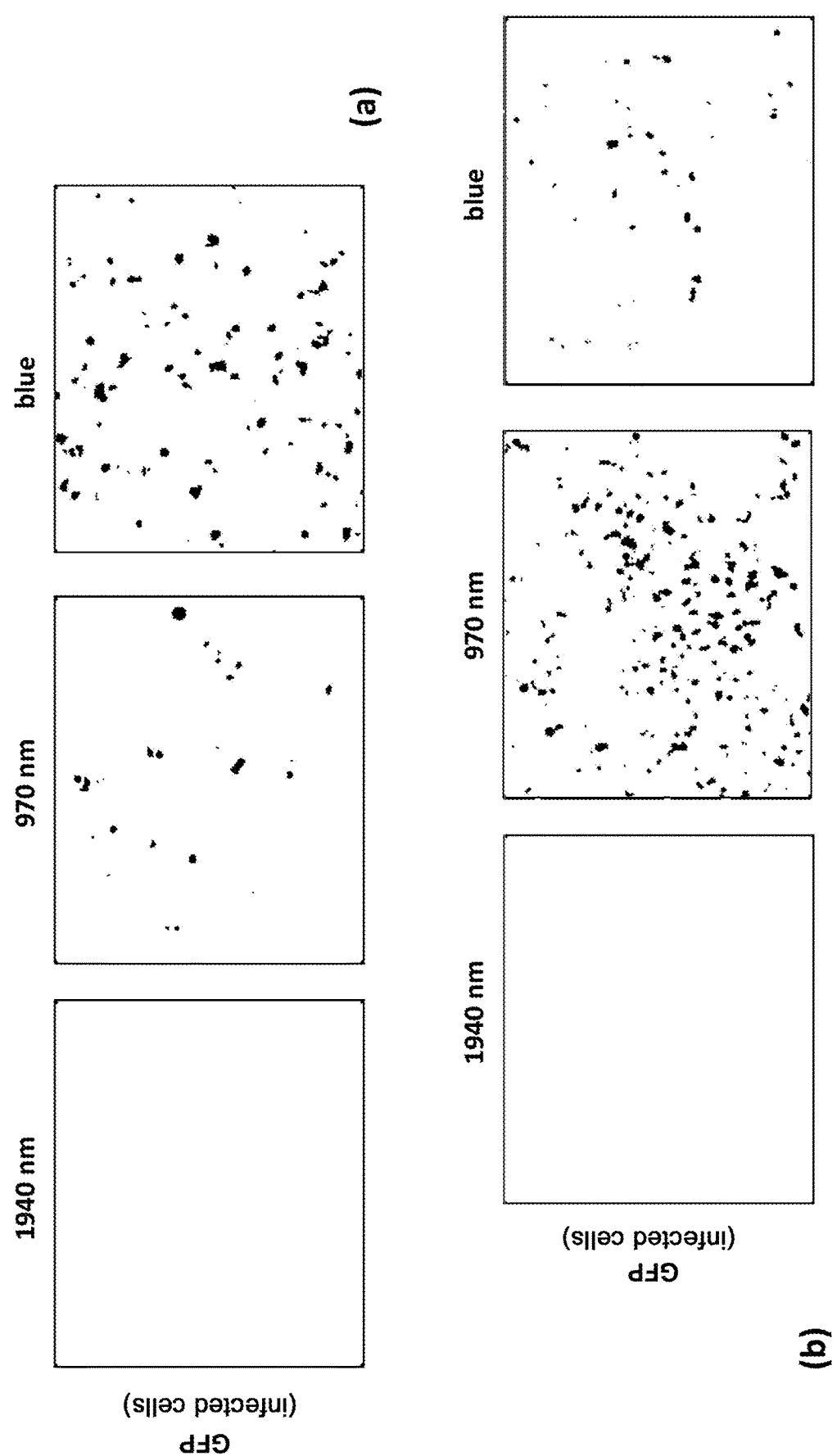
FIG. 13 shows a fourth test of three different wavelengths, with high irradiance.

As shown in FIG. 13(a), the three results are compared to the three wavelengths for the AAV, while in (b) the three results are compared for the Lentiviral. It is easily concluded that only the 1940 nm wavelength, despite a significantly lower irradiance than the others, achieved the total destruction of the viruses.

Test No. 5—Test with IR Laser with Different Irradiances

Having found that the ideal wavelength is 1940 nm, the following tests served to calculate the minimum irradiance needed to destroy the viruses in 1 second.

Figure 14:
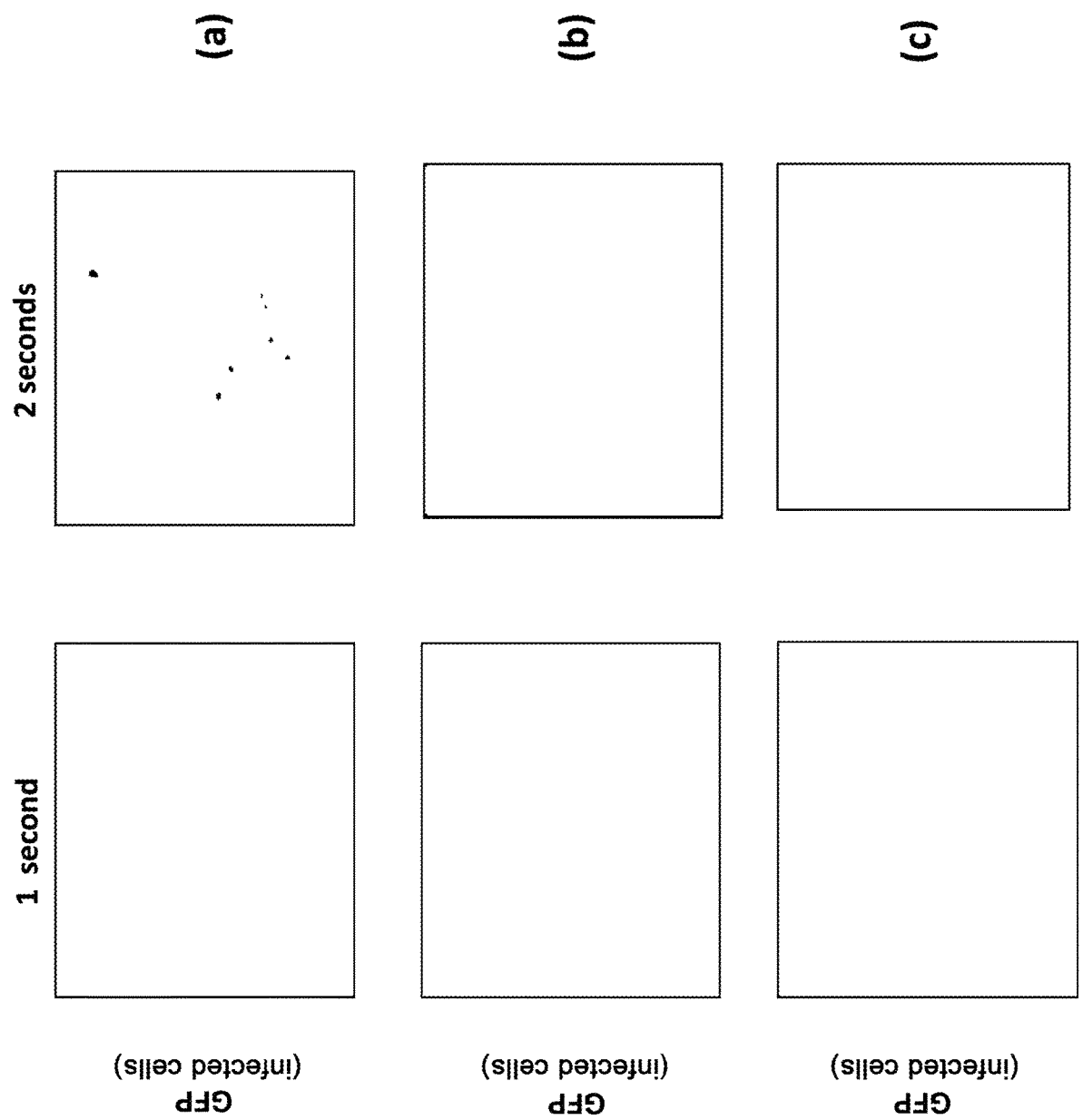
FIG. 14 shows a fifth test with 1940 nm IR Laser but with different irradiances than those in FIG. 12.

Referring to FIG. 14, in this test three first different irradiances occurred, with only 2.5 W of laser source power, in an exposure time of 1 and 2 seconds with all three different irradiances:
 (a) 35.7 W/cm², 3 mm spot diameter (0.07 cm²)
 (b) 9.8 W/cm², 6 mm spot diameter (0.28 cm²)
 (c) 3.9 W/cm², 9 mm spot diameter (0.63 cm²)

The viruses used were (recovery of small drops around the Eppendorf tube using the cellular medium):
 HEK293T; 5K for 96 wells (15k cells/cm²)-1 drop of virus (1 µL) in Eppendorf tube;

Lentiviral vector—GFP (10× preparation) in Eppendorf tube (drop of 1 μL).

In all three cases the complete destruction of the viruses was achieved.

Test No. 6—Further Tests with IR Laser with Different Irradiances

Referring to FIG. 15, the irradiance used at the 1940 nm wavelength was 3.9 W/cm$^2$ (9 mm in diameter, 0.63 cm$^2$), 2.65 W/cm$^2$ (spot: 11 mm in diameter, 0.94 cm$^2$), 1.9 W/cm$^2$ (spot: 13 mm in diameter, 1.32 cm$^2$) 1.4 W/cm$^2$ (spot: 15 mm in diameter, 1.76 cm$^2$) for just one second of exposure.

The viruses used were (recovery of small drops around the Eppendorf tube using the cellular medium):

HEK293T; 5K for 96 wells (15k cells/cm$^2$)–1 drop of virus (1 μL) in Eppendorf tube+spin down Lentiviral vector—GFP (10× preparation), added in an Eppendorf tube (drop of 1 μL)

The results of the test show that with a laser at 1940 nm the destructive effect of the virus is obtained and with safety up to an irradiance of only 1.9 W/cm$^2$ in just one second of exposure.

Test No. 7—Further Tests with IR Laser at 10600 nm

Referring to FIG. 16, in this series of tests the lentiviral vector—GFP is used, irradiated with a laser at 10600 nm and three different irradiances: 5.6; 14 and 24 W/cm$^2$. It can be seen from the figure, compared to the control with infected cells, that all three irradiances are effective in completely destroying the viral load.

Test No. 8—Test with Lentiviral Vector in Aerosol

Figure 17:
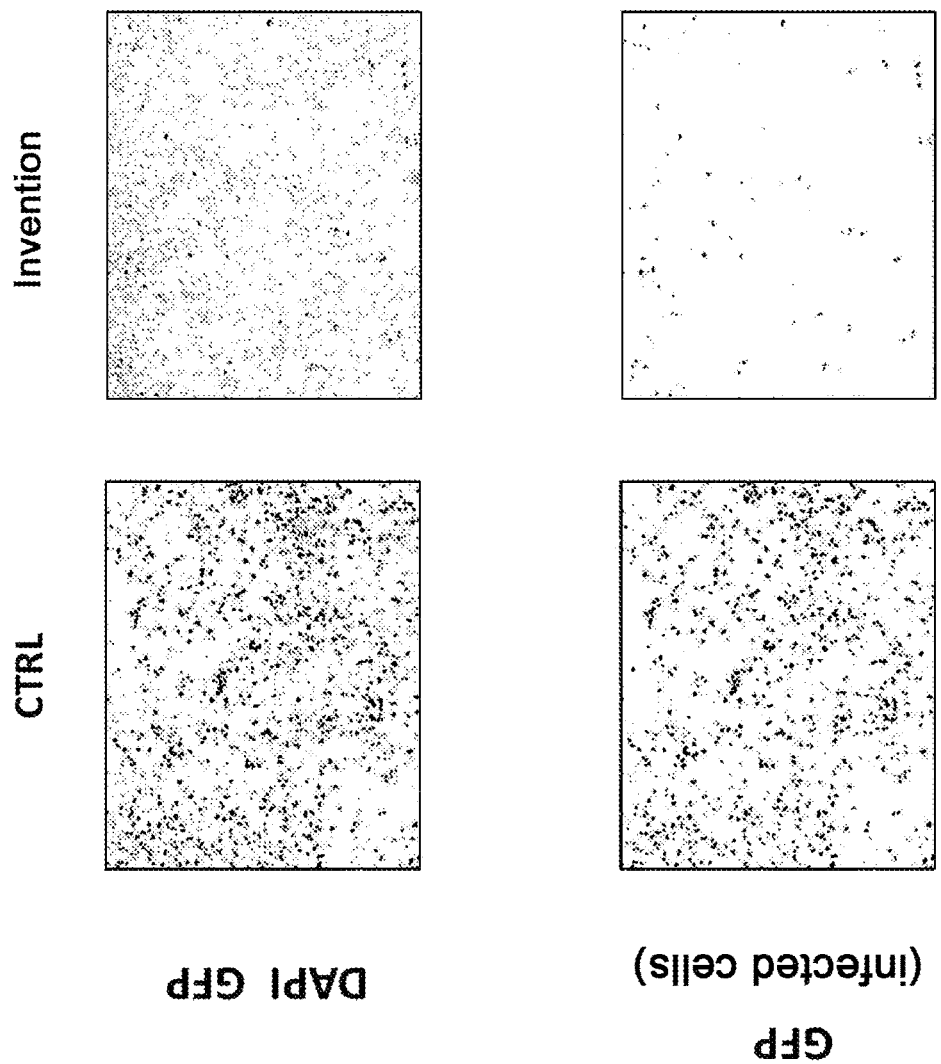
FIG. 17 shows an example of the antiviral effect of the device of the present invention on the GFP lentiviral vector: the images are representative of HEK293T cells, infected with the vector, 48 hours after infection, in the untreated version (two figures on the left, one colored with DAPI) and treated (two figures on the right, one colored with DAPI). The GFP lentiviral vector in solution was nebulized, collected, and plated with the cells. The aerosol was treated for 15 msec with the device according to the invention (Treated, gray bar) or not (Untreated Ctrl, black bar) before being added to the cells. In the left panels, the presence of biologically active virus in the aerosol is demonstrated by the massive positivity of the cells to GFP. The antiviral effect of the laser device according to the invention on the GFP lentiviral vector is shown in the right panel, in which very few cells test positive for infection. Separate channels on the lower panels emphasize the infected cells (green)

FIG. 17 shows an example of the antiviral effect of the device of the present invention on the GFP lentiviral vector: the images are representative of HEK293T cells, infected with the vector, 48 hours after infection, in the untreated version (two figures on the left, one colored with DAPI) and treated (two figures on the right, one colored with DAPI).

The GFP lentiviral vector in solution was nebulized, collected, and plated with the cells. The aerosol was treated for 15 msec with the device according to the invention (in which there was only one laser beam) before being added to the cells. In the left figures, the presence of biologically active virus in the aerosol is demonstrated by the massive positivity of the cells to GFP. The antiviral effect of the laser according to the invention on the GFP lentiviral vector is shown in the right panel, in which very few cells test positive for infection.

Figure 18:
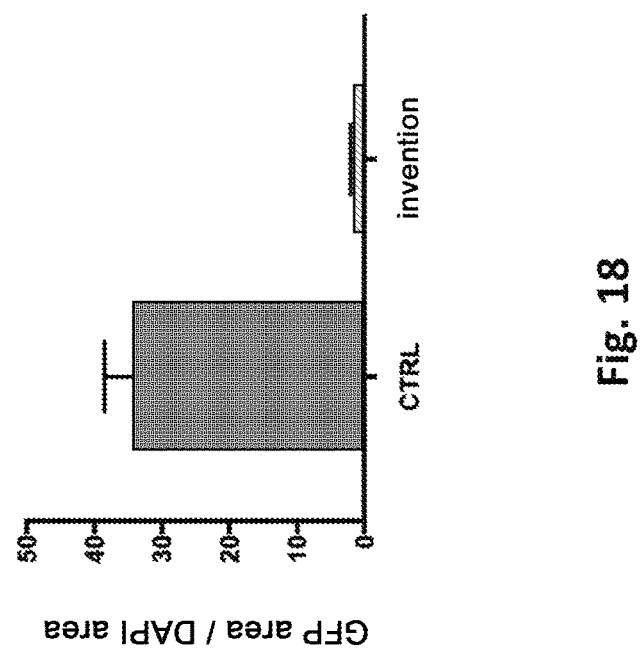
FIG. 18 shows an example of the effect of the device according to the invention: the quantification of the area covered by normalized GFP cells on the DAPI area is shown.

FIG. 18 quantifies the effect: the quantification of the area covered by normalized GFP+ cells on the DAPI area is shown (clearer nuclei in FIG. 17). The antiviral effect of the device according to the invention is significantly demonstrated by the poor presence of cells infected with GFP (less than 2%) versus control (untreated—CTRL), in which the infection rate reaches 40% of the cells. The data are shown as a mean±S.E.M. The statistical significance was determined using the so-called "unpaired" Student's t test.

Test No. 9—Test with *Legionella* in Aerosol

Figure 19:
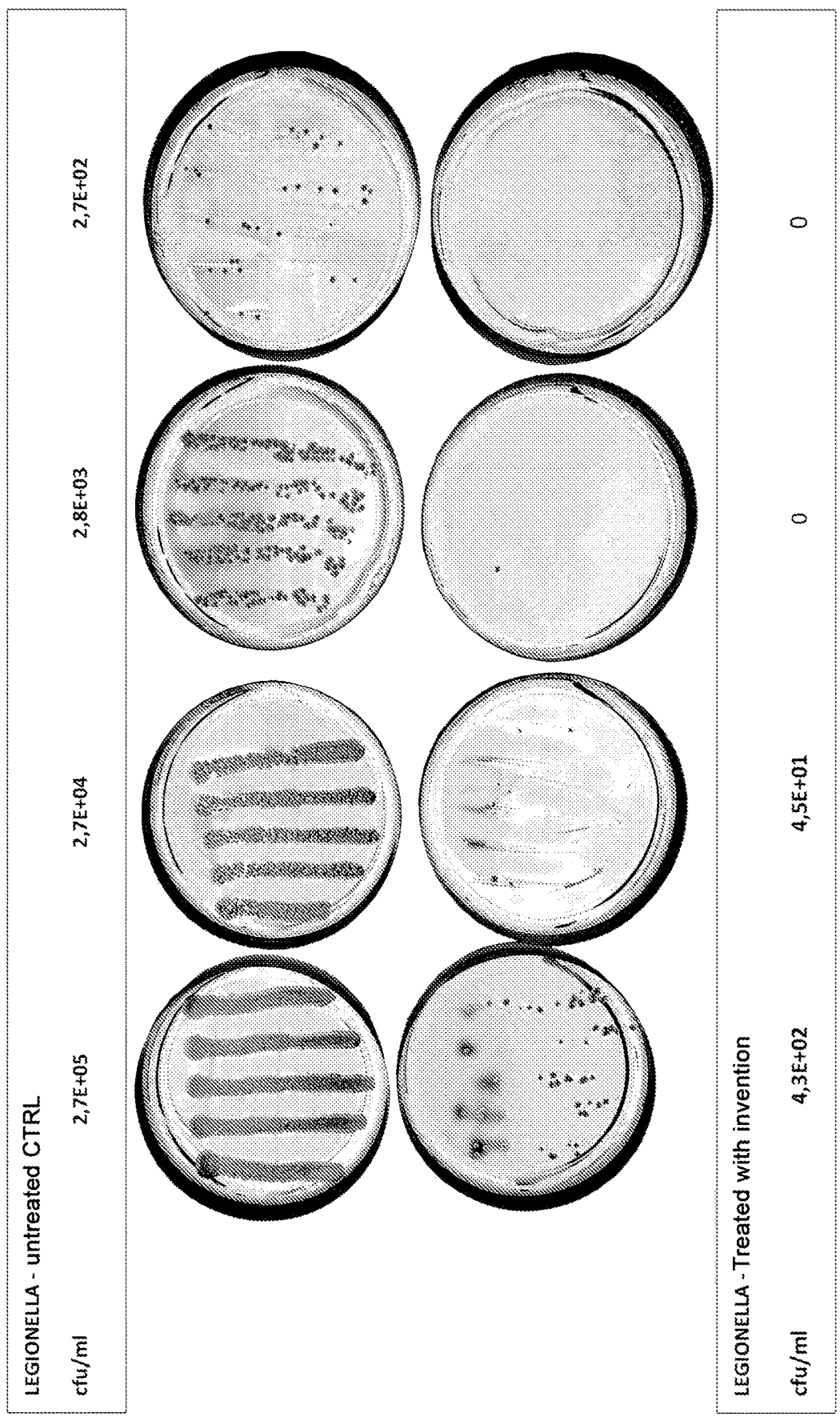
FIG. 19 shows an antimicrobial effect of the device according to the invention on *Legionella pneumophila* in aerosol; the images are representative of the bacteriological strips for quantification of *Legionella pneumophila* 4 days after deposition on the plate.

FIG. 19 shows an antimicrobial effect of the device according to the invention on *Legionella pneumophila* in aerosol. The images are representative of the bacteriological strips for quantification of *Legionella pneumophila* 4 days after deposition on the dish.

A sample of *Legionella pneumophila* in solution was nebulized, collected, and placed on Petri dishes. The generated aerosol was treated for 15 msec with a prototype of the device of the invention (treated) and untreated (untreated—CTRL). It should be specified here that only one laser beam was used in the prototype, but more laser beams can be used (therefore with a longer exposure time) to increase the efficacy of the sterilization. This consideration is valid for any type of sterilization, including those of the other tests reported in the present description.

As shown in the leftmost images, the presence of viable bacteria in the aerosol is demonstrated by the formation of actively growing colonies on the slides, especially the untreated ones (CTRL). The antimicrobial effect of the laser of the device according to the invention on *Legionella pneumophila* is shown on the lower dishes (dishes with treated material), in which only a few colonies are visible. The total count of live *Legionella pneumophila* cells after treatment with the device of the invention is also shown in the figure. The number of live *Legionella pneumophila* bacteria is significantly reduced by three orders of magnitude.

Test No. 10—Test with Sars-Cov-2 in Aerosol

Tests were carried out to verify the antiviral effect of the device according to the invention on Sars-CoV-2 viruses in aerosols.

The quantification of the viruses was performed 72 hours after the infection and the laser treatment according to the invention. Sars-CoV-2 virus in solution was nebulized, collected, and deposited on plates on primate Vero cells. The generated aerosol was treated for 15 msec with a prototype of the device according to the invention and compared with an untreated control sample. While the untreated sample showed a PFU/ml amount of $5.5 \times 10^3$, the treated sample showed a reduced PFU/ml amount of $7 \times 10^2$, therefore with an 87% reduction of the virus in just 15 ms of treatment.

It should also be specified here that only one laser beam was used in the prototype, which is already very effective, but more laser beams can be used (therefore with a longer exposure time) to increase the efficacy of the sterilization.

Further Embodiments Using the Venturi Effect

Figure 20:
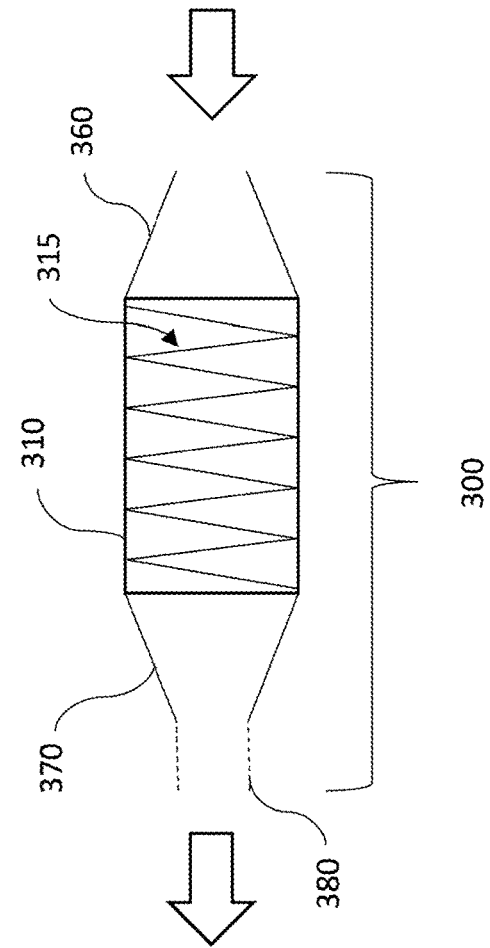

Referring to FIG. 20, during the research and testing, the Inventor found an unexpected effect using the Venturi effect in conjunction with the above laser sterilization. The two means work in synergy, ensuring a great improvement of the sterilization efficacy even with low laser powers.

Basically, in the device 300 the central body 310 is the chamber in which the laser grid 315 is developed as described above. Means 360, 370 are placed at the inlet and/or outlet of the central body 310 for restricting the volume towards the respective mouths of the central body, so that the volume increases away from the central body. This causes a Venturi effect, i.e., an acceleration of the airflow (large arrows) inside the central body with a simultaneous increase in pressure in the ducts 360 and/or 370. The increase in pressure was found to affect the survival of viruses, while it is less relevant for that of bacteria. At the outlet of the device according to the invention, after the enlargement 370 a conduit 380 with substantially constant section can be placed. The device 300 can be multiplied, i.e., multiple devices 300 can be connected in a row to increase the effects on sterilization.

Figure 21:
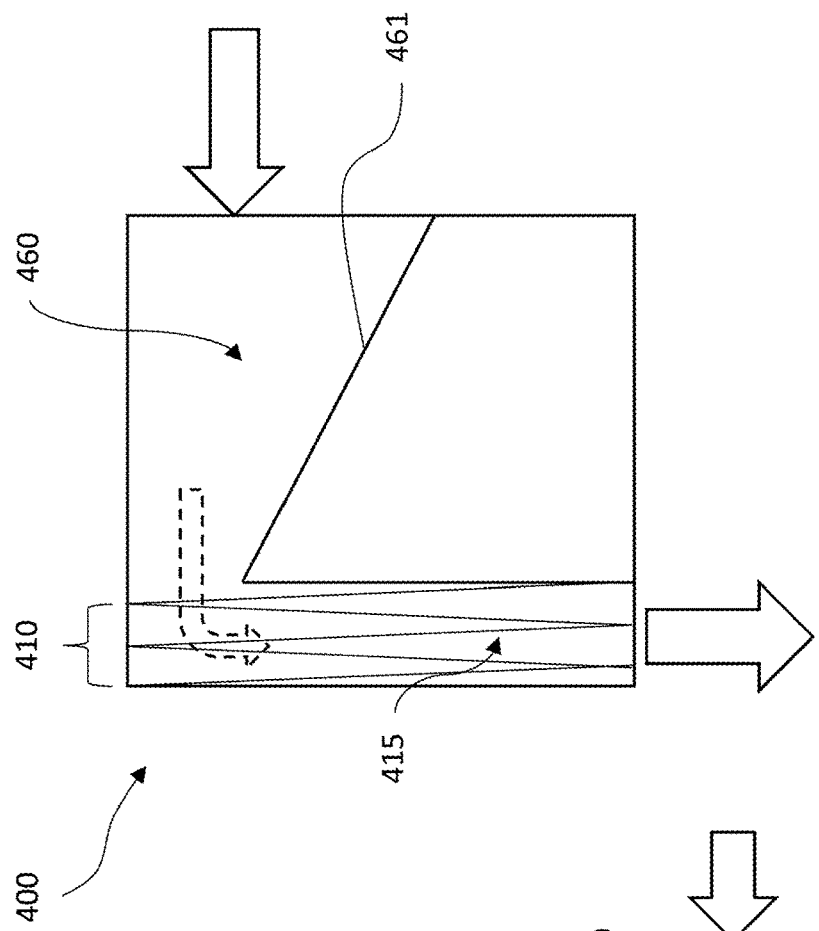

A variation of such an embodiment is shown in FIG. 21, in which the device 400 has a narrowing 461 at the inlet 460 to the chamber 410 of the laser grid 415. The laser grid, as in the other embodiments, can be created with vertical beams, i.e., which run along the extension of the chamber 410. An enlargement similar to 370 can be placed at the outlet of the device to increase the sterilization efficacy. Compared to the embodiment in FIG. 19, in this case the airflow goes through a right angle before reaching the laser, with constructional advantages in terms of compactness and costs.

The inventor deduces that the increased pressure is able to destroy the viral materials, known to be weak, with particular synergy and efficacy if the laser is used as described. The materials weakened by one are completely destroyed by the other, regardless of the order of application.

Advantages and Applications

The present invention consists of a device which adopts a sustainable architecture, through innovative design and technology which allow it to be optimized in multifunctional use, providing for example the following advantages:

- installability in spaces for the public transport of people or food or non-food goods,
- possibility of covering large walls or very long corridors with a small footprint and without taking room away from the space;
- no preparation of the premises is necessary before or after installation;
- weight reduction in relative and absolute terms;
- installability on public transport vehicles;
- installability on food transport vehicles;
- installability on medical emergency vehicles;
- installability in medical clinics, public waiting rooms, cinemas, theaters, shops, department stores, supermarkets, workspaces, meeting rooms, medical, craft or industrial laboratories of all kinds;
- installability on boats, ships of all kinds;
- rooms and living rooms, such as hotels, spas, locker rooms and sports areas, gyms, and all public places where food is handled, bars and restaurants included;
- installability on airliners and private aircraft, public and private transport, and cargo aircraft;
- installability in all public offices, ministries, banks, insurance companies and similar places, especially where there is a greater concentration of people;
- installability in airports or railway or maritime stations;
- installability in refrigerated counters where food is stored;
- very easy to install in elevators, a likely contagion point among people.
- installability in private spaces, civil homes;
- reduction of electricity consumption compared to traditional sterilizers, through the ultrasonic sensor system which regulates power when it senses the presence of people in the vicinity;
- ease and practicality of use ("user friendly") with no major contraindications;
- long product life and reduced maintenance.

In no case of the prior art air was subjected to great laser light exposure energy for a stable time ≥500 ms, as can instead be achieved by the present invention.

In addition to the advantages listed above, the installation space is recovered, and can be used for multiple functions, including contemporary ones, such as:

- advertising services;
- general and emergency notices;
- graphics or artistic paintings;
- fixing LCD or OLED or any other active computer screen or entertainment screen; and
- incorporation of speakers or mono or stereo sound system.

The device according to the invention can destroy any virus or bacterium or insect, and in particular among the viruses:

- Influenza virus type A and B
- Respiratory Syncytial Virus (RSV)
- Human parainfluenza viruses
- Rhinovirus
- Adenovirus
- Coronavirus
- Enterovirus
- Human metapneumovirus and among the bacteria:

- *Bordetella pertussis* and *Bordetella parapertussis*
- *Chlamydia pneumoniae*
- *Mycoplasma pneumoniae*

As well as insects carrying the following diseases:

- Zika,
- sleeping sickness,
- malaria,
- Leishmaniasis,
- West Nile virus,
- Yellow fever,
- Japanese encephalitis,
- Tuscany virus encephalitis,
- Dengue,
- Chikungunya The present invention is not only capable of destroying the virus in just one second, but can be used with maximum safety and without contraindications, precisely in case of presence of people, in any space by aspirating aerosol and sterilizing it in only one second. Therefore, it finds application in all spaces, being fixed or movable, such as any means of transport, buses, ships, airplanes, etc.

It does not produce any polluting material for disposal and requires maintenance every 24 months. It may be transported with supports provided with wheels, hung from the ceiling, either leaned or hung on the wall, and in any dynamic position. It does not require special technical installations, simply a connection to a universal low-voltage electricity source: 100-240 VAC 50/60 Hz. It consumes about 100 W/h depending on the size of the model to be installed.

According to an aspect of the invention, the device described and claimed is capable of measuring the concentration of droplets present in the space where the device is installed and the proximity or presence and concentration of people present in the space by means of suitable sensors. This allows the device to activate dynamically, adjusting the action intensity thereof in a very dynamic manner, saving energy and lengthening the lifetime of the wearable parts. Due to this "smart" use, the electric power absorbed varies from a few tens of watts to peaks of 600 W.

The preferred embodiments and possible variants of the present invention have been outlined above, but it is to be understood that those skilled in the art may make modifications and changes without thereby departing from the scope of protection, as defined in the appended claims.

The invention claimed is:

1. A device for-sterilizing a gas, comprising:

a sterilization chamber with an inlet and an outlet and a flow direction between said inlet and said outlet;

a ventilation system configured to let the gas flow from said inlet to said outlet;

one or more sources of at least one laser beam positioned so that said at least one laser beam passes through said sterilization chamber; wherein:

said at least one laser beam has a wavelength alternatively in a range of +15% around 1940 nm, 2950 nm, 9300 nm, or 10600 nm, and a predetermined irradiance;

the sterilization chamber comprises a system of mirrors configured to create a network of laser segments inside the sterilization chamber;

said laser segments are incident with respect to said flow direction; and said ventilation system is configured to let the gas flow with a speed which depends on the number of said laser segments, on the wavelength and on said predetermined irradiance of said at least one laser beam;
and wherein:
said at least one laser beam is introduced in said sterilization chamber with a first inclination (alpha) from 0.2 to 1° or from 1 to 15° with respect to a direction perpendicular to said flow direction;
said at least one laser beam is introduced at a first end of the sterilization chamber along said flow direction and is reflected by at least one respective mirror inclined at a second end of the sterilization chamber along said flow direction, opposite to said first end, with a second inclination (B) from 0.2 to 1° or from 1 to 15° with respect to said perpendicular direction, wherein said second inclination differs from said first inclination.

2. The device of claim 1, wherein said gas is air.

3. The device of claim 1, wherein said one or more laser sources have an overall average power from 1 to 1000 W CW.

4. The device of claim 1, wherein said ventilation system is configured to let said gas flow between said inlet and said outlet at a speed between 0.5 and 5 m/s or between 5 and 10 m/s.

5. The device of claim 1, wherein before said inlet and/or after said outlet an additional funnel-shaped chamber is placed, to create a Venturi effect in said sterilization chamber and a pressure increase in the volume in the additional funnel-shaped chamber.

6. The device of claim 1, wherein the system of mirrors is configured so that, after said first inclination (a), said at least one laser beam is alternatively reflected with a path perpendicular to the flow direction and with an inclination between 1 and 15° with respect to said perpendicular direction again, and similarly after said second inclination (B).

7. The device of claim 1, wherein said sterilization chamber has a substantially parallelepiped shape, wherein length is along said flow direction, bases perpendicular to said flow direction include said inlet and said outlet, respectively, and the smaller sides along said flow direction have a predetermined thickness which is a function of a thickness of said at least one laser beam.

8. The device of claim 7, wherein said predetermined thickness is a multiple of said thickness of said at least one laser beam.

9. The device of claim 7, wherein said system of mirror comprises at least one portion of surface reflecting said at least one laser beam, said at least one portion of surface facing the interior of the sterilization chamber and being positioned on said smaller sides.

10. The device of claim 1, wherein said sterilization chamber has a substantially cylinder shape, in which height is along said flow direction, said inlet and said outlet are along a side wall, and the bases comprise said system of mirrors, said one or more sources of at least one laser beam being positioned so that said at least one laser beam passes through said sterilization chamber in a height direction.

11. The device of claim 1, wherein after said one or more sources of the at least one laser beam, at least one respective beam expander is placed, configured to reduce divergence of the at least one laser beam to a value between 0.3 and 1 mrad and increase a surface of the at least one laser beam to a size comparable to that of the mirrors of said system of mirrors.

12. The device of claim 1, wherein gas deflection means are provided at said inlet, configured to convey the gas towards the center of said sterilization chamber as viewed perpendicularly to said flow direction.

13. The device of claim 1, wherein around at least one portion of an outer wall of said sterilization chamber, a collector of said gas is assembled, fluidly connected to said inlet.

14. The device of claim 1, wherein said first inclination (alpha) is between 0.2 to 1° or from 1° to 5 degrees.

15. The device of claim 1, wherein said one or more laser sources have an overall average power between 1 and 30 W CW.

16. The device of claim 1, wherein said second inclination (B) is between 0.2 and 5 degrees.

\* \* \* \* \*